US009204938B2

(12) United States Patent
Duhamel et al.

(10) Patent No.: US 9,204,938 B2
(45) Date of Patent: *Dec. 8, 2015

(54) VISUALIZATION GUIDED ACL LOCALIZATION SYSTEM

(71) Applicant: Smith & Nephew, Inc., Andover, MA (US)

(72) Inventors: Paul Robert Duhamel, Groton, MA (US); Carlos Rodriguez, Wakefield, MA (US); Charles H. Brown, Wellesley, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/714,562

(22) Filed: May 18, 2015

(65) Prior Publication Data

US 2015/0245880 A1    Sep. 3, 2015

Related U.S. Application Data

(63) Continuation of application No. 14/288,932, filed on May 28, 2014, and a continuation of application No. 12/967,435, filed on Dec. 14, 2010, now Pat. No. 8,860,757.

(60) Provisional application No. 61/327,416, filed on Apr. 23, 2010, provisional application No. 61/286,170, filed on Dec. 14, 2009.

(51) Int. Cl.
*G06T 11/00* (2006.01)
*A61B 19/00* (2006.01)
(Continued)

(52) U.S. Cl.
CPC ............ *A61B 19/50* (2013.01); *A61B 1/00045* (2013.01); *A61B 1/317* (2013.01);
(Continued)

(58) Field of Classification Search
None
See application file for complete search history.

(56) References Cited

U.S. PATENT DOCUMENTS 4,839,822 A    6/1989    Dormond et al.
5,968,050 A    10/1999    Torrie
(Continued)

FOREIGN PATENT DOCUMENTS

CN    101160104 A    4/2008
WO    2006091494 A1    8/2006
WO    2007/136770 A3    11/2007

OTHER PUBLICATIONS

Clinical User Guide Rev. 1.1, VectorVison ACL Ver. 1.0, Dec. 31, 2006, BrainLAB AG, Germany, XP002629725, pp. 28-31, pp. 93-108.

Petermann, J. et al., Computer-Assisted Planning and Robot-Assisted Surgery in Anterior Cruciate Ligament Reconstruction, Operative Techniques in Orthopaedics, vol. 10, No. 1, Jan. 2000, XP002629726.

Shafizadeh S. et al., Die Computer-Unterstutzie Kreuzbandrekonstruktion, SFA, Arthroskopie aktuall, Dec. 31, 2002 (incl. English translation).

(Continued)

*Primary Examiner* — Andrew Yang
(74) *Attorney, Agent, or Firm* — Chapin IP Law, LLC

(57) ABSTRACT

A computerized system provides assistance for placement of localization markers for medical operations such as ACL repair procedures. The system displays, on a graphical user interface, an image of an anatomical structure and allows identification, via an input device on the graphical user interface, of a set of landmark locations identifying respective anatomical positions within the displayed image of the anatomical structure. The system displays a graphical overlay over the image of the anatomical structure. Placement of the graphical overlay is based on the set of landmark locations. The system displays at least one localization marker within the graphical overlay. The localization marker(s) identify a location for performing a surgical operation associated with the anatomical structure, such as ACL repair surgical operations.

42 Claims, 17 Drawing Sheets

(51) Int. Cl.
*G06T 7/00* (2006.01)
*A61B 1/00* (2006.01)
*A61B 5/00* (2006.01)
*A61B 1/317* (2006.01)

(52) U.S. Cl.
CPC .............. *A61B 5/7264* (2013.01); *A61B 19/56* (2013.01); *G06T 7/0012* (2013.01); *A61B 2019/507* (2013.01); *A61B 2560/0475* (2013.01); *A61B 2576/02* (2013.01); *G06T 2200/24* (2013.01); *G06T 2207/30008* (2013.01)

(56) References Cited

U.S. PATENT DOCUMENTS

| | | |
|---|---|---|
| 6,346,940 B1 | 2/2002 | Fukunaga |
| 7,259,731 B2 | 8/2007 | Allen et al. |
| 7,427,200 B2 | 9/2008 | Noble et al. |
| 8,471,866 B2 | 6/2013 | Friedman et al. |
| 2004/0105086 A1 | 6/2004 | Leitner et al. |

OTHER PUBLICATIONS

International Search Report mailed Apr. 20, 2011 in corresponding International Application No. PCT/US2010/060256.
CPEL1252119P English Language Translation of Office Action including Search Report and OAI translation for P.R. China Application No. 201080063789.5.
P.R. of China First Office Action for P.R. China Application No. 201080063789.5, Oct. 11, 2014.
"BrainLab neurosurgery solutions", ПopTфoИЯo HeЙpox Я pyprЯ И, 2006, BrainLab AG, Germany, extracted from Internet on Oct. 13, 2014 at http://www.belmedtorgservis.com/uploaded/brainlab/nevro.pdf, p. 11.
Russian Office Action for Application No. 20128424/14(04543) Dec. 15, 2014.
Second Japanese Office Action, Japanese Application No. 2012-544707, dated May 25, 2015 (citation No. 1 previously identified by Applicants in subject US patent application).
Chinese Second Office Action, Dated Jun. 2, 2015, 25 pages. (D1 and D2 previously cited).
Australian Patent Examination Report No. 1, Dated Jun. 18, 2015, 3 pages. (D1 and D2 previously cited).

VISUALIZATION GUIDED ACL LOCALIZATION SYSTEM

CROSS-REFERENCE TO RELATED APPLICATIONS

This application is a continuation of U.S. patent application Ser. No. 14/288,932, filed May 28, 2014 (Now Allowed), entitled VISUALIZATION GUIDED ACL LOCALIZATION SYSTEM; which application is a continuation of U.S. patent application Ser. No. 12/967,435, filed Dec. 14, 2010, entitled VISUALIZATION GUIDED ACL LOCALIZATION SYSTEM, which application claims priority to U.S. Provisional Application No. 61/327,416, entitled COMPUTER ASSISTED VISUALIZATION AND PLACEMENT OF LOCALIZATION MARKERS FOR MEDICAL PROCEDURES, filed Apr. 23, 2010, and U.S. Provisional Application No. 61/286,170, entitled VISUALIZATION GUIDED ACL LOCALIZATION SYSTEM, filed Dec. 14, 2009. Each of these applications is incorporated herein by reference in its entirety.

FIELD

The invention relates to the area of computerized assistance and visualization in determining placement of localization markers for use in surgical operations.

BACKGROUND

Modern medical technologies including computerized imagery and endoscopy technologies have significantly advanced the field of arthroscopic medicine. In particular, in the area of arthroscopic surgical procedures, conventional computerized devices are able to render real-time live x-ray views of anatomical structures undergoing a medical procedure. One example of a common medical procedure is the repair of soft tissue, such as the anterior cruciate ligament (ACL), within a person's knee joint. A damaged ACL is often replaced arthroscopically by a tissue graft. The tissue graft can be harvested from a portion of a patellar tendon having so called "bone blocks" at each end or from the semitendonosis and gracilis. Alternatively, the tissue graft can be formed from synthetic materials or from a combination of synthetic and natural materials. The replacement tissue graft is implanted by securing one end of the tissue graft in a tunnel formed in a passage within the femur, and passing the other end of the graft through a tunnel formed in the tibia. Generally, sutures are used to affix each end of the tissue graft to an anchor (e.g., an interference screw or a post), which is then secured to the bone. Identification of the specific locations for placement of the tunnels in the femur and tibia of a knee joint can be somewhat tricky given that the knee joint is a dense area and there are many different sized bones for different people undergoing the ACL repair procedure.

One example of a mechanical device that provides assistance in properly locating the ACL insertion sites is described in issued U.S. Pat. No. 5,968,050 (the '050 patent) which is issued to the same assignee as the present application. The entire contents of the '050 patent is hereby incorporated by reference in its entirety. The '050 patent describes a purely physical guide or tool for positioning a tibial tunnel in ACL reconstruction. As opposed to a physical tool, another example of a conventional technology used for ACL reconstruction utilizes real-time x-ray and computerized graphical imagery to assist in ACL repair procedures for a knee joint and is described in U.S. Pat. No. 7,319,897 (hereinafter the '897 patent), the entire teachings and contents of which are hereby incorporated by reference in their entirety.

Conventional mechanisms that provide computer-aided assistance for surgical techniques such as the one described in the '897 patent suffer from a variety of deficiencies. A computerized system, methods and apparatus that provide localization software operable to allow a medical professional such as a surgeon to view both still and video frames of images of an anatomical structure on a graphical user interface are needed.

SUMMARY

Embodiments disclosed herein provide a computerized system, methods and apparatus that provide the needed localization software described above. The images may be obtained from equipment that produces a radiographical (e.g. x-ray) image, a magnetic resonance image, a computerized tomography image, fluoroscopic image, or the like. The images may be live real-time images obtained intra-operatively, or may be prerecorded imagery being used post operatively (e.g. for quality control purposes). The software allows for the identification, on the graphical user interface, of a set of landmark locations identifying respective anatomical positions within the displayed image of the anatomical structure. The surgeon can manually identify such landmarks via interaction with the GUI, or the software can use an auto-detect function to automatically locate or identify landmark locations within the anatomical structure. As an example, if the anatomical structure is a knee joint, the system can display an image (e.g. x-ray) of the knee joint and allow the surgeon to select specific known bone locations within the x-ray image as the landmark locations in relation to the femur or tibia.

Upon selection of the landmark locations, the system is operable to display a graphical overlay such as an overlay grid or line over the image of the anatomical structure. Placement of the graphical overlay is based on the set of landmark locations. The surgeon is able to select one of a set of specific graphical overlays rendered by the system and the graphical overlay can include a series of guidance indicators operable to indicate positions associated to the anatomical structure for performing the surgical operation associated with the anatomical structure. The guidance indicators can, for example, indicate percentage positions providing a distance metric or scale across the distance between the landmark locations of the bone. The system is then operable to display at least one localization marker within the graphical overlay. The localization marker(s) identify an optimal location for performing a surgical operation associated with the anatomical structure. The placement of the localization marker(s) can be performed by the system by using medically recognized positions in relation to the anatomical structure (based on the landmark location) to allow for maximum success of the medical procedure such as ACL repair.

In one embodiment specific to ACL insertion location determination, the system is operable to display an image showing a view of a femur and tibia within a human knee joint. This includes displaying a lateral view of the femur within a human knee joint. The system receives a selection of known bone locations. This includes receiving, as the first known bone location, a selection of an anterior edge of the view of the femur displayed within the image, and receiving, as a second known bone location, a selection of a posterior edge of the view of the femur displayed laterally within the image. A line defined between the first known bone location and the second known bone location defines a plane that substantially aligns with a patellar surface of the femur. The system receives a selection of a third known bone location corresponding to the laterally displayed distal condyle surface of the femur within the image. When displaying the graphical overlay over the image of the anatomical structure, the system displays an overlay grid over the view of the distal end of the femur within the graphical user interface. The overlay grid has a width rendered between the selected first and second known bone locations, and has a height that extends to the selected third known bone location. The system is further operable to displaying at least one femoral localization marker within the overlay grid. The femoral localization marker identifies a reference location for a tissue graft insertion site within the femur displayed within the graphical image.

In other embodiments, when displaying a localization marker the system can automatically calculate at least one medically preferred position within the overlay grid for placement of the localization marker based on a geometry of the overlay grid and can display a respective localization marker at each automatically calculated medically preferred position within the overlay grid. Once the auto-placed localization marker(s) have been placed, the system allows a medical professional to adjust the automatically calculated placement of a respective localization marker within the overlay grid.

In knee joint specific embodiments, for the tibia, the system is operable to display a lateral view of the tibia within a human knee joint and receive, as the first known bone location, a selection of an anterior edge of the tibia displayed within the image. The system also receives, as the second known bone location, a selection of a posterior edge of the view of the tibia displayed laterally within the image. For the tibia, the line defined between the first known bone location and the second known bone location defines a plane upon where at least one localization marker can be displayed for repair of a ligament associated with the tibia. Upon selection of the landmark locations associated to the tibia, the system displays an overlay line over the view of the proximal end of the tibia within the graphical user interface between the two tibia landmark locations. Once the overlay line is rendered, the system is operable to display at least one tibia localization marker located upon the overlay line. The tibia localization marker(s) identifies at least one anatomic ACL insertion site on the tibia displayed within the graphical user interface.

In this manner, embodiments disclosed herein provide for more accurate surgical procedures or other medical operations since rendering of the graphical overlays over the anatomical structures allows for accurate placement of localization markers that enable precise placement of medical tasks such as tissue graft site location determination. The guidance indicators within the overlay grids provide medically accepted locations for placement of the localization markers and avoid a doctor misplacing a marker.

Other embodiments disclosed herein include any type of computerized device, workstation, handheld or laptop computer, or the like configured with software and/or circuitry (e.g., a processor) to process any or all of the method operations disclosed herein. In other words, a computerized device such as a computer or a data communications device or any type of processor that is programmed or configured to operate as explained herein is considered an embodiment disclosed herein.

Other embodiments disclosed herein include software programs to perform the steps and operations summarized above and disclosed in detail below. One such embodiment comprises a computer program product that has a computer-readable medium including computer program logic encoded thereon that, when performed in a computerized device having a coupling of a memory and a processor, programs the processor to perform the operations disclosed herein. Such arrangements are typically provided as software, code and/or other data (e.g., data structures) arranged or encoded on a computer readable medium such as an optical medium (e.g., CD-ROM), floppy or hard disk or other a medium such as firmware or microcode in one or more ROM or RAM or PROM chips or as an Application Specific Integrated Circuit (ASIC). The software or firmware or other such configurations can be installed onto a computerized device to cause the computerized device to perform the techniques explained herein as embodiments disclosed herein.

It is to be understood that the system disclosed herein may be embodied strictly as a software program, as software and hardware, or as hardware alone and may be used standalone or in conjunction with other systems such as medical devices for obtaining real-time live video of x-rays of an anatomical structure.

BRIEF DESCRIPTION OF THE DRAWINGS

The foregoing and other objects, features and advantages disclosed herein will be apparent from the following description of particular embodiments disclosed herein, as illustrated in the accompanying drawings in which like reference characters refer to the same parts throughout the different views. The drawings are not necessary to scale, emphasis instead being placed upon illustrating the principles disclosed herein.

DETAILED DESCRIPTION

In general, the system disclosed herein operates as software with a localization host computer system that operates (e.g. executes) localization software (e.g. application and/or process) that can display video (e.g. live real-time radiographic images) of an anatomical structure and that allows a medical professional, such as a surgeon to accurately determine a proper location for performance of a surgical task associated with a medical procedure in relation to the displayed anatomical structure. This processing can be done intra-operatively to assist in determining a location for performance of some aspect of a surgical operation that is in progress, or post-operatively such as may be used for quality control purposes. The localization application enables, via interaction with the graphical user interface, selection of specific landmark locations on the anatomical structure (e.g. specific bone locations visible within the displayed image). In response, the localization software displays a graphical overlay based on the placement of the selected landmark locations.

The graphical overlay can be, for example, an overlay grid having visible graphical indicators such as scales, rulers, segments, metrics or the like to assist the medical professional in determining proper location of localization markers to be placed within the image (in relation to the grid). With the graphical overlay in place, the medical professional is able to further interact with the graphical user interface to position and display one or more localization markers that identify the location for performing the surgical operation associated with the anatomical structure. In one specific example embodiment, the localization software performs the above summarized processing to display at least one femoral and/or tibial localization marker within the overlay grid. Such femoral and/or tibial localization markers identify reference location(s) for a tissue graft insertion site within the femur or tibia displayed within the graphical image.

Figure 1:
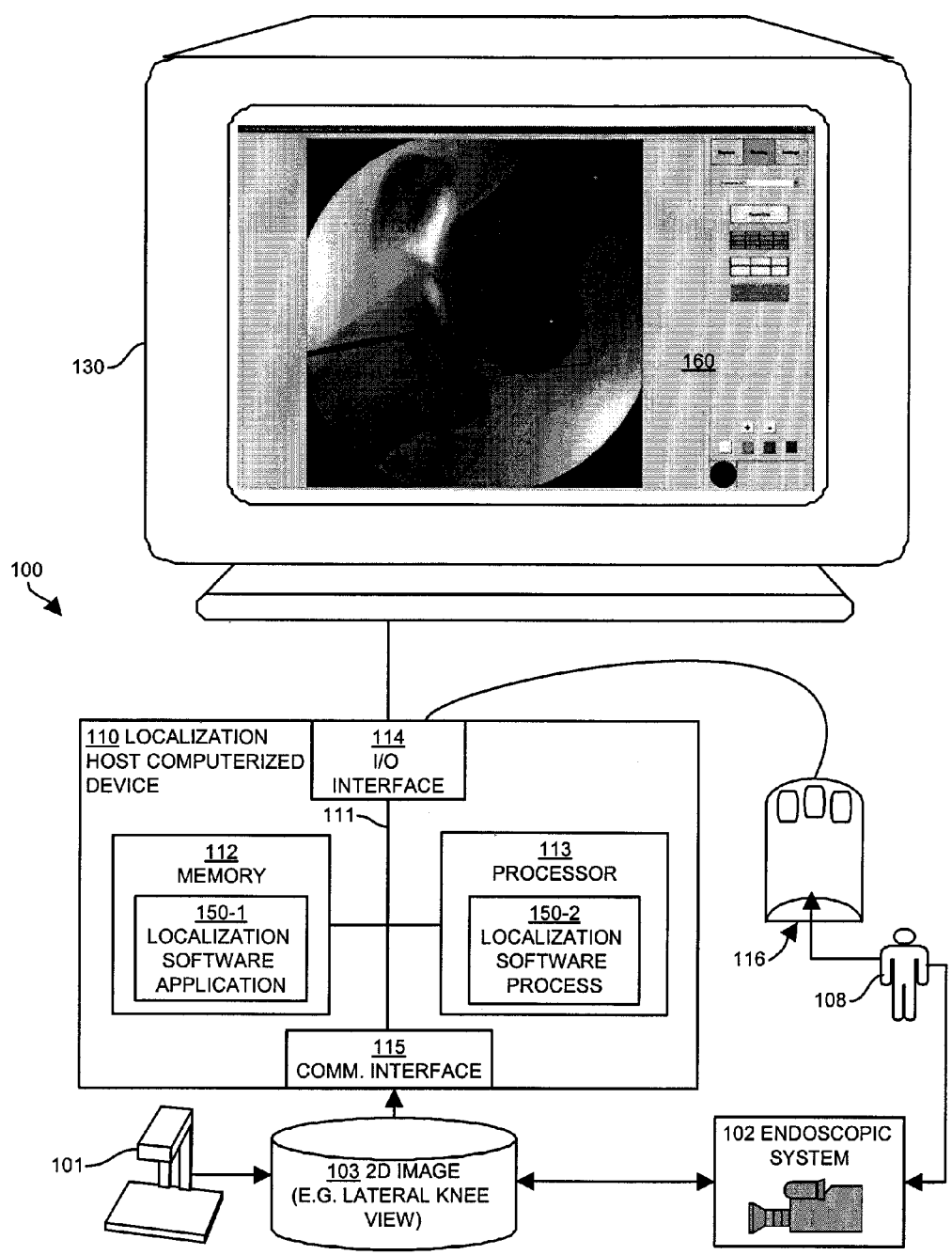
FIG. 1 shows a high-level block diagram of a medical computing system environment configured according to one embodiment disclosed herein.

FIG. 1 illustrates a medical environment 100 suitable for use in explaining details of operation of example embodiments of the invention. The environment 100 includes medical imaging device 101 such as a magnetic resonance imaging (MRI) system, a computerized tomography (CT) system, a fluoroscopy system, a Radiographic (e.g. x-ray) system or similar system that produces image data 103 that includes a two-dimensional (2D) lateral video image view of an anatomical structure. In this example, the medical imaging device 101 produces a 2D lateral image of a human knew joint. The environment 100 can alternatively include an endoscopic system 102 that can provide internal views of the anatomical structure and that can also produce the image data 103. A localization host computer system 110 receives the image data 103 (e.g. via a video/frame capture device) and is operable to render the image data 103 within a graphical user interface 160 on a display 130.

The localization host computer system 110 may be any type of computerized device such as a personal computer, workstation, portable computing device, console, laptop, network terminal or the like. As shown in this example, the computer system 110 includes an interconnection mechanism 111 such as a data bus or other circuitry that couples a memory system 112, a processor 113, an input/output interface 114, and a communications interface 115. One or more input devices 116 (e.g., user controlled devices such as a mouse, keyboard, touch screen, touchpad, etc.) couple to the processor 113 through the input/output interface 114 and enable a user 108 such as a medical professional (e.g. Doctor, surgeon, etc.) to provide input commands and generally control the graphical user interface 160 containing the image data 103 on the display 130, as will be explained. The communications interface 115 enables the computer system 110 to communicate with other devices (i.e., other computers) on a network (not shown).

The memory system 112 is any type of computer readable medium and in this example is encoded with a localization application 150-1 that supports processing and functional operations via the graphical user interface 160 as explained herein. The localization application 150-1 may be embodied as software code such as data and/or logic instructions (e.g., source or object code stored in the memory or on another computer readable medium such as a removable disk) that supports processing functionality according to different embodiments described herein. During operation of the localization computer system 110, the processor 113 accesses the memory system 112 via the interconnect 111 in order to launch, run, execute, interpret or otherwise perform the logic instructions of the localization application 150-1. Execution of the localization application 150-1 in this manner produces processing functionality in a localization process 150-2. In other words, the localization process 150-2 represents one or more portions or runtime instances of the localization application 150-1 (or the entire application 150-1) performing or executing within or upon the processor 113 in the computerized device 110 at runtime.

The localization application 150-1 may be stored on a computer readable medium (such as a floppy disk), hard disk, electronic, magnetic and optical or other computer readable medium. The localization application 150-1 may also be stored in the memory system 112 such as in firmware, read only memory (ROM), or, as in this example, as executable code in, for example, Random Access Memory (RAM). It is to be understood that reference to the localization software 150 is a general reference to either the localization application 150-1 in the memory 112, and/or the executing localization process 150-2 executing on the processor 113. Those skilled in the art will further understand that the localization host computer system 110 may include other processes and/or software and hardware components, such as an operating system not shown in this example. The display 130 need not be coupled directly to computer system 110. For example, the localization software 150 can be executed on a remotely accessible computerized device via the communications network interface 115. In this instance, the graphical user interface 160 may be displayed locally to a user of the remote computer and execution of the processing herein may be client-server based. Further disclosure of details of the operation of the localization software 150 will now be explained with respect to the remaining figures that show flow charts of processing steps explained in conjunction with screenshots of the graphical user interface 160 provided by the localization software 150.

FIGS. 2 through 5 provide a flow chart of processing steps that the localization software 150 performs in accordance with example embodiments disclosed herein. For this example discussion, the system will be explained for use of determining placement of localization markers that identify reference locations for the tissue graft insertion sites within a femur and tibia. It is to be understood that this medical procedure is provided by way of example only and that the invention is not limited to this procedure or procedures on knee joints. Rather, certain embodiments of the invention are intended to be general in nature and applicable to assisting in identifying locations for medical procedures associated with many different anatomical structures. The flowchart will be explained with reference to a graphical user interface 160 shown in the remaining figures.

Figure 5:
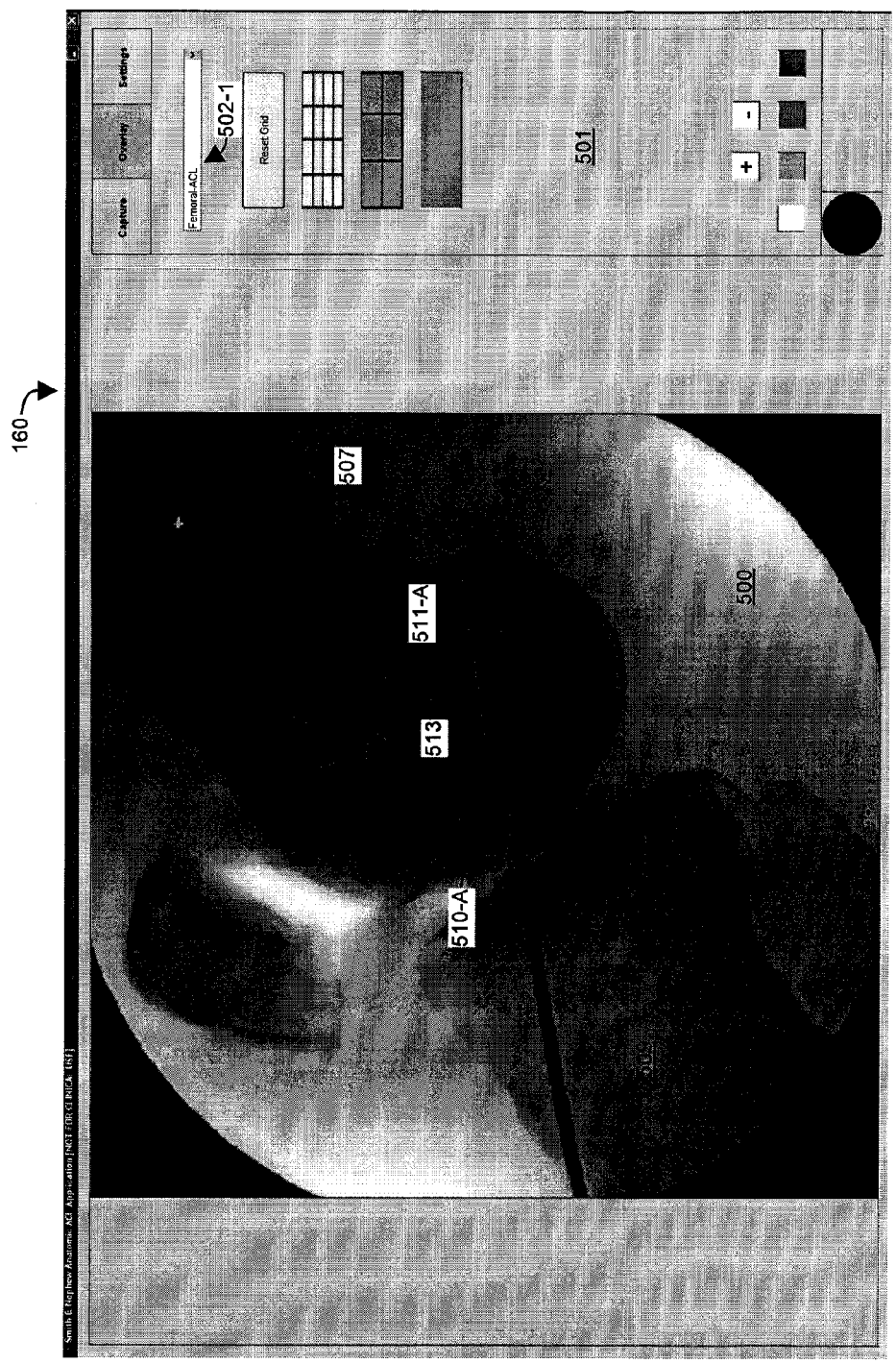
FIG. 5 shows a graphical user interface for displaying images produced by the medical imaging device.

Referring ahead briefly to FIG. 5, the graphical user interface 160 includes an image area 500 that is operable to display images such as video and/or still frames of radiographical or other images produced by the medical imaging device 101 or endoscopic system 102 from FIG. 1. The interface 160 also includes a control area 501 that includes various controls that will be explained during the following description. Note that steps in the flowcharts shown within other steps represent sub-steps performed according to various example embodiments as disclosed herein.

Figure 2:
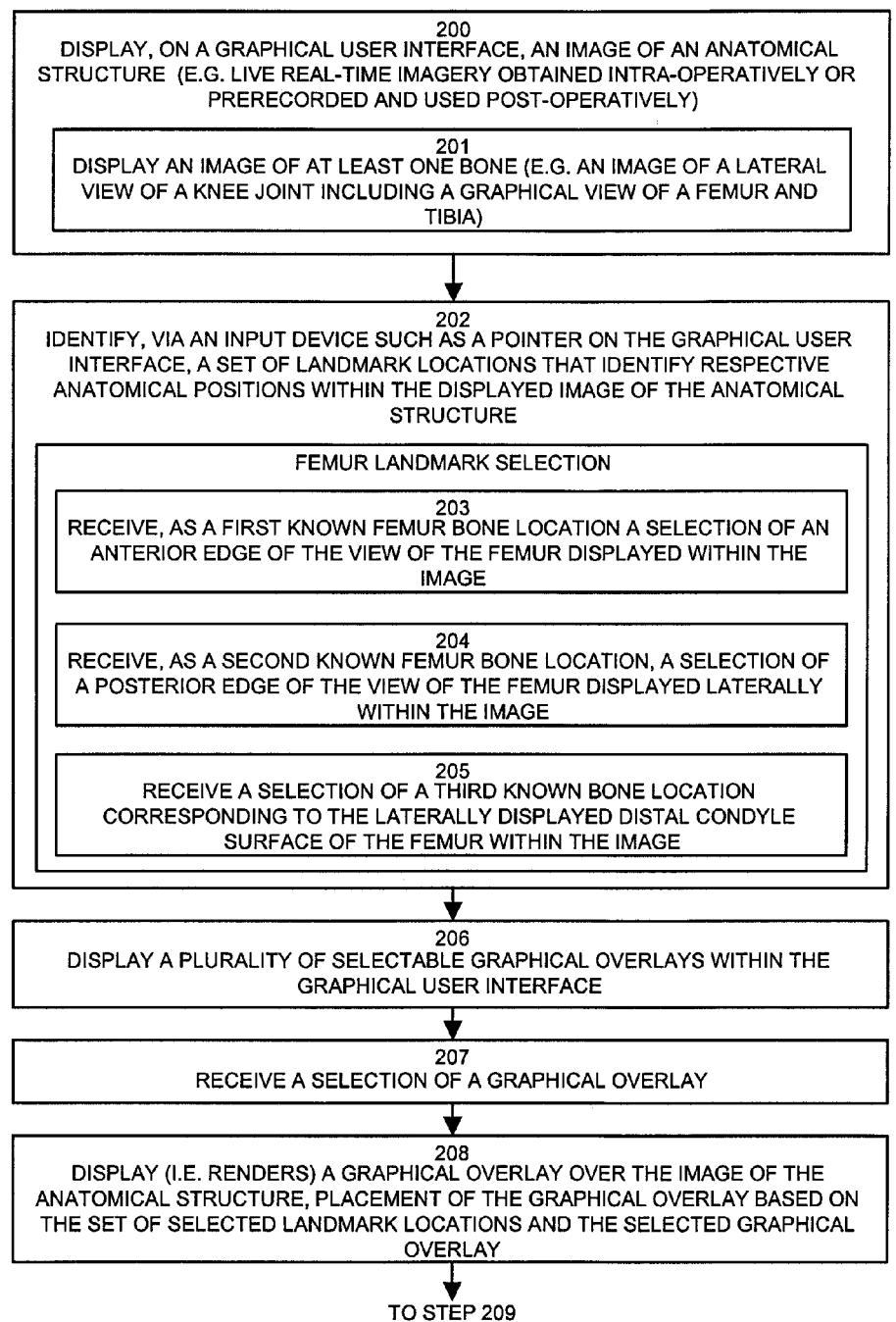
FIGS. 2 through 4 show flow charts of processing steps performed in accordance with example embodiments disclosed herein.
Figure 3:
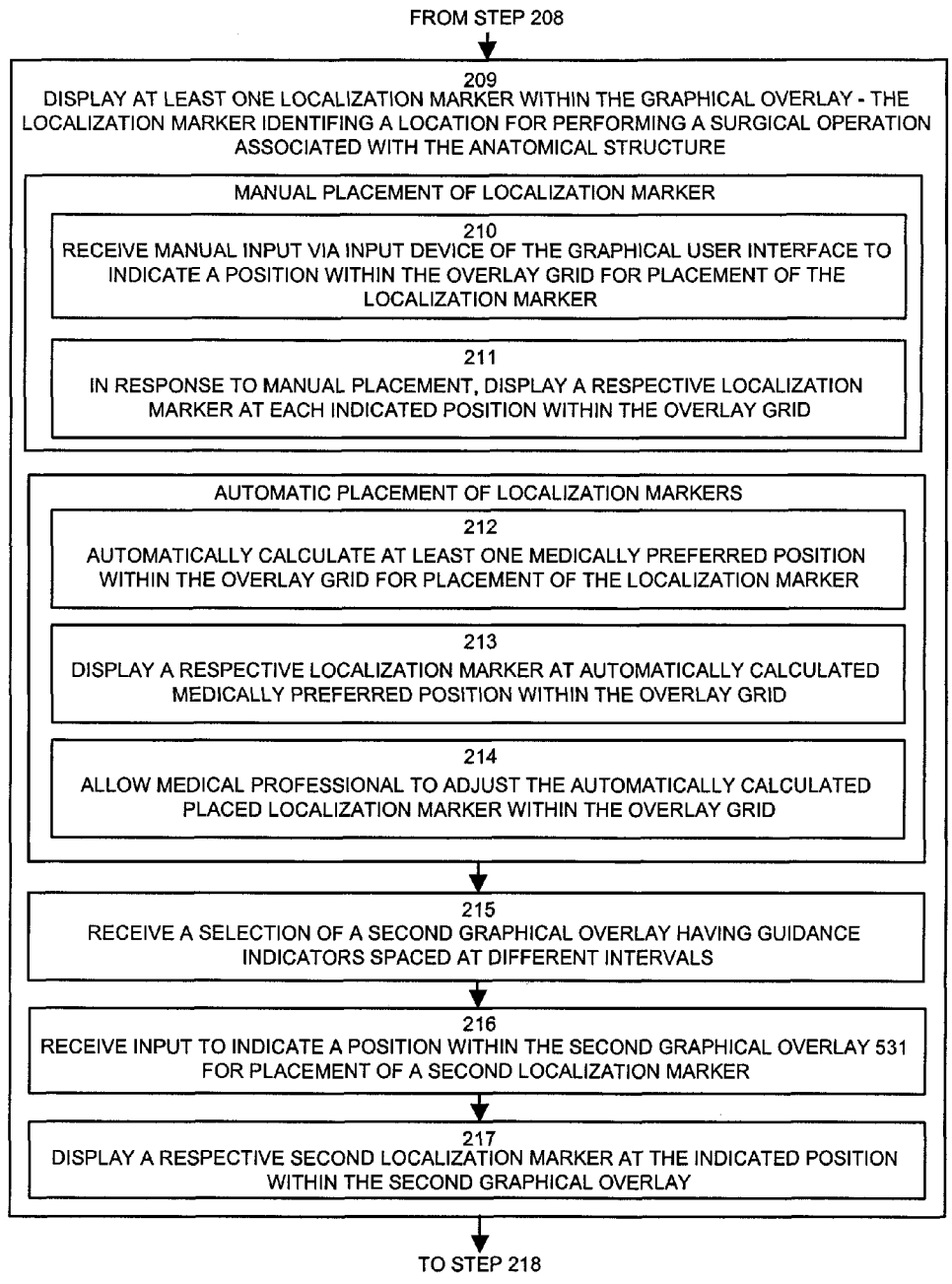
Figure 4:
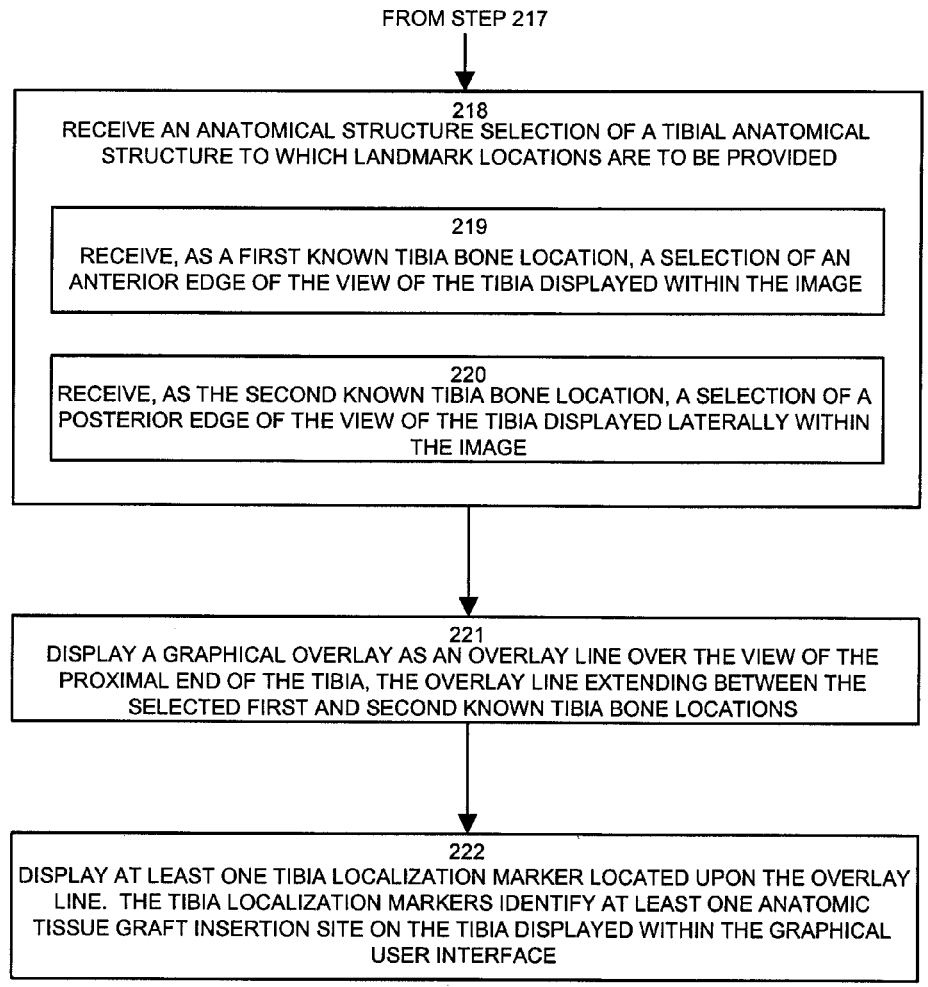

Referring back to the flowchart in FIG. 2, in step 200 the localization software 150 displays, on a graphical user interface 160 (i.e. within the image area 500), an image of an anatomical structure. The image may be, for example, live real-time imagery obtained intra-operatively during a medical procedure, or may be prerecorded and the processing described herein may be performed post-operatively.

In sub-step 201 the localization software 150 displays an image of the anatomical structure including an image of at least one bone. In this particular example, the image area 500 displays an image of a lateral view of a knee joint including a graphical view of a femur 507 and tibia 509.

In step 202 the localization software 150 identifies, via an input device such as a pointer on the graphical user interface, a set of landmark locations 510, 511 identifying respective anatomical positions within the displayed image of the anatomical structure. In the example in FIG. 5, the localization software 150 receives an anatomical structure selection 502 of a specific anatomical structure to which landmark locations are to be provided. In this example, the surgeon has selected a Femoral-ACL structure 502-1 and as such, the localization software is configured to receive a selection of three known bone locations for the femur 507 displayed within the image area 500.

The processing sub-steps 203 through 205 relate to landmark locations selected for a femur 507.

In sub-step 203, for determining a reference location associated to the femur, the localization software 150 receives, as a first known bone location 510-A, a selection of an anterior edge (at location 510-A) of the view of the femur 507 displayed within the image. This landmark location is shown in FIG. 5 as location 510-A. As noted, the surgeon can use the mouse or other input device 116 to operate a pointer on the graphical user interface 160 to select the first landmark location 510-A. As an example, the surgeon can use his or her knowledge of the anatomy in the image area 500 to select the first landmark location.

In sub-step 204 the localization software 150 receives, as the second known bone location 511-A, a selection of a posterior edge of the view of the femur 507 displayed laterally within the image. A line 513 defined between the first known bone location 510-A and the second known bone location 511-A is drawn as the surgeon moves the pointer from the first to the second location. This line 513 extends (e.g. as a vector) from the first set landmark location 510-A and graphically tracks the pointer as it moves across the image 500 prior to final selection of the second landmark location 511-A. This line 513 enables the surgeon to visualize where a top edge of a graphical overlay will reside once the final landmark selection is made using the system.

Figure 6:
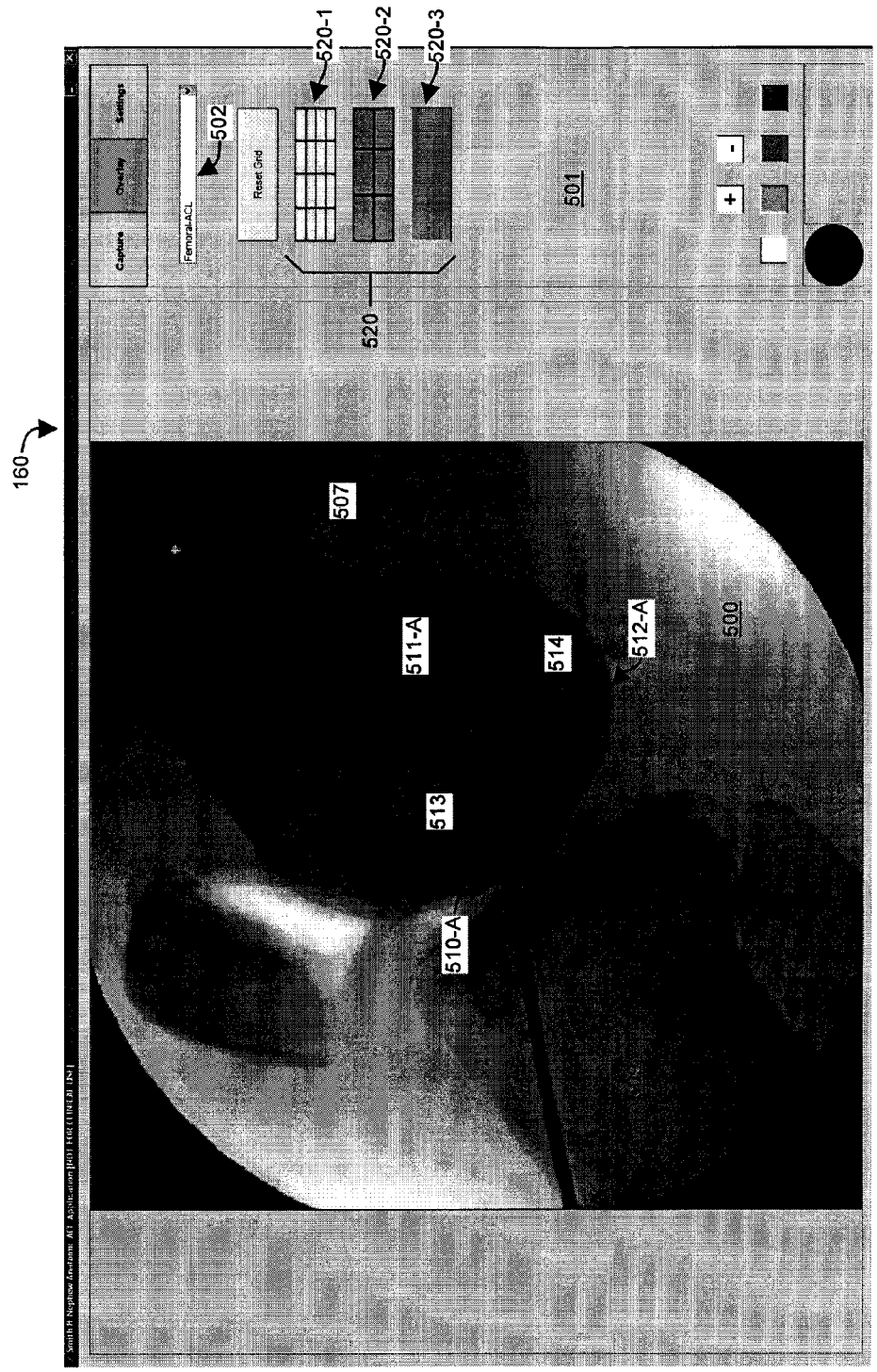
FIGS. 6 through 17 show example embodiments of a graphical user interface showing specific steps and processing operations described within the flow charts from FIGS. 2 through 4.

In sub-step 205, the localization software 150 receives a selection of a third known bone location 512-A. Referring to FIG. 6, for the femur 507, after selecting the first and second locations 510-A and 511-A, in sub-step 205 the localization software 150 receives a selection of a third known bone location 512-A corresponding to the laterally displayed distal condyle surface of the femur 507 within the image. Note as the surgeon moves the pointer towards each successive landmark location 510-A, 511-A, 512-A, prior to selection of that next landmark location itself, the localization software 150 is continually rendering an image of the line from the previous landmark location. In the case of the line 514 for the third landmark location for a femur 507, the line 514 extends perpendicularly away from the line 513 as the surgeon moves to pointer towards the distal end of the femur 507 (i.e. below the graphical line 513 which is now fixed in place between the two previously selected landmark locations 510-A and 511-A). This perpendicular line 514 provides the surgeon with a visual indication, on the graphical user interface 160 (i.e. within the image 500), of the geometry of the graphical overlay that will be produced upon completing selection of the final (i.e. third) landmark location 512-A for the displayed femur 507. In other words, after selecting the second anatomical point as a second landmark location 511-A, a second line extends (as a dotted line) perpendicular to the line now defined between the two landmark locations 510-A and 511-A. This line 514 is used to align the first line so it is perpendicular to the tibial longintudinal axis. Upon selection of the third landmark location, the overlay is rendered. In this manner, the system is operable to provide visual indicators (lines 513 and 514) of where the overlay will reside.

In step 206 the localization software 150 displays a plurality of selectable graphical overlays within the graphical user interface 160. In FIG. 6, the selectable graphical overlays are shown as 520-1, 520-2, and 520-3 (collectively referred to as 520). Each graphical overlay 520 provides a respective series of guidance indicators (differently spaced apart grid lines in this example) that are operable to indicate scaled positions associated to the anatomical structure for performing a respective portion of the surgical operation associated with the anatomical structure.

In step 207 the localization software 150 receives a selection of a graphical overlay (e.g. 520-1) from a plurality of available graphical overlays 520. The surgeon may select an overlay of his or her choice at any time. Selection of a particular overlay 520 is based on what specific reference location is being determined for repair, in this example, of an ACL. In particular, for an ACL repair procedure using a double bundle, the graphical overlay 520-1 having guidance indicators at 25% increments allows for placement of a first marker at a known location (i.e. 25% over and 25% down from the upper right corner of the displayed overlay grid 530) for localizing the Anteriomedial (AM) bundle based on medical literature concerning this procedure. The graphical overlay 520-2 can be selected for proper localization marker placement of the Posteriolateral (PL) bundle, which is typically understood in the medical profession to be placed 33% over and 50% down from the upper right corner of the overlay grid. It is to be understood that the overlays 520-1 and 520-2 can be used properly position a marker for a single bundle as well. Note that the previous steps 206 and 207 for selecting a particular graphical overlay 520 can be performed prior to selecting landmark locations in steps 203 to 205 however no graphical overlay 520 will be rendered prior to selection of landmark locations.

In step 208, after completion of selection of landmark locations, the localization software 150 displays (i.e. renders) a graphical overlay 520 over the image of the anatomical structure, placement of the graphical overlay based on the set of landmark locations and the selected graphical overlay 520. Generally, in this example, the graphical overlay 530 is rendered and enables ease of determination of at least one reference location to be marked by the at least one localization marker for performing a surgical operation related to repair of a ligament of the human knee joint.

Figure 7:
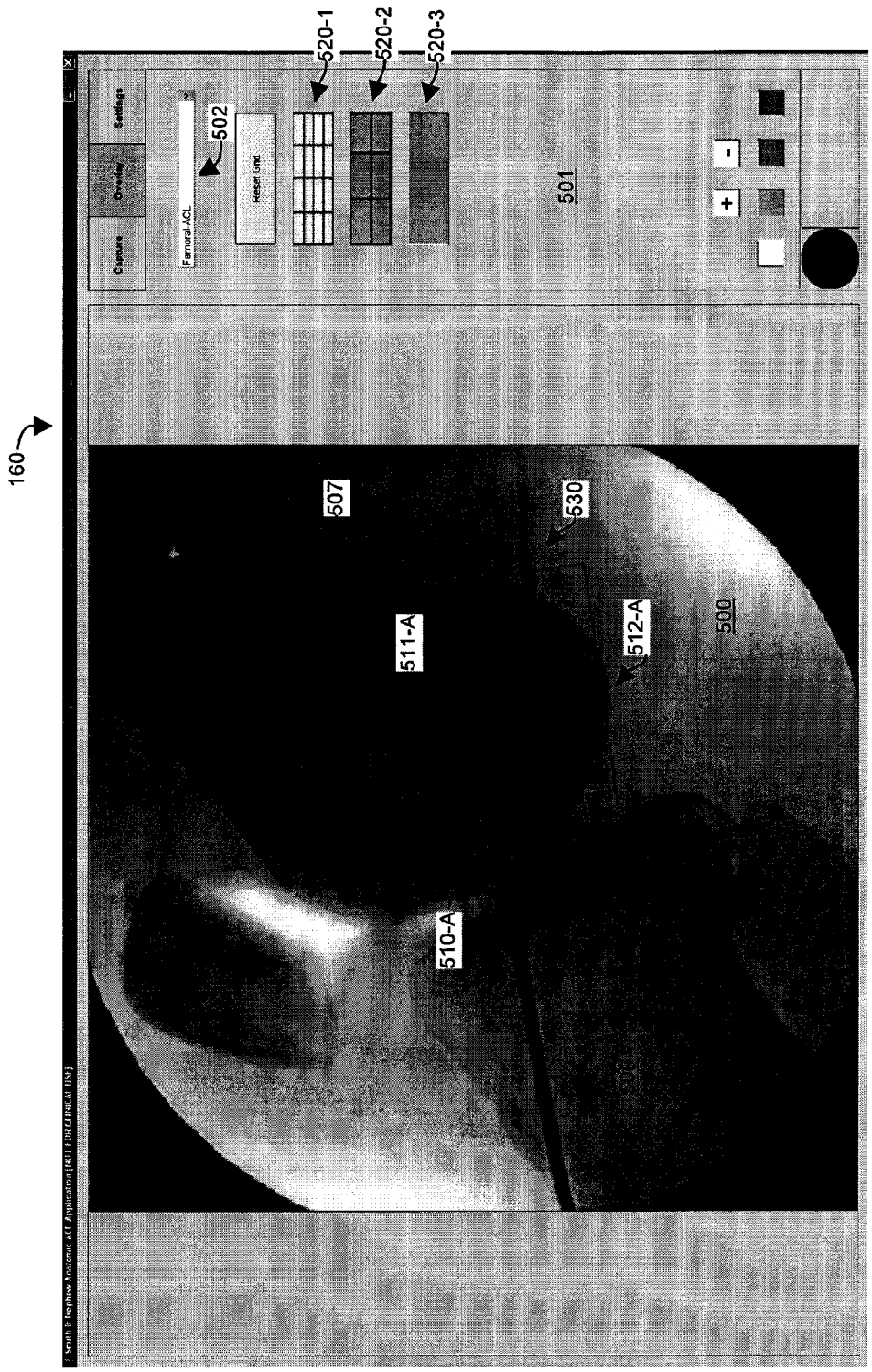

FIG. 7 shows an example of the graphical user interface 160 after the user (i.e. surgeon) has selected graphical overlay 520-1 (shown guidance indicators at 25% increments between the landmark locations) and after selection of the landmark locations. In this example, the localization software 150 displays the overlay grid 520-1 over the lateral view of the femur 507 within the graphical user interface. The overlay grid 520 has a width rendered between the selected first and second known bone locations 510-A, 511-A, and has a height that extends to the selected third known bone location 512-A.

Figure 8:
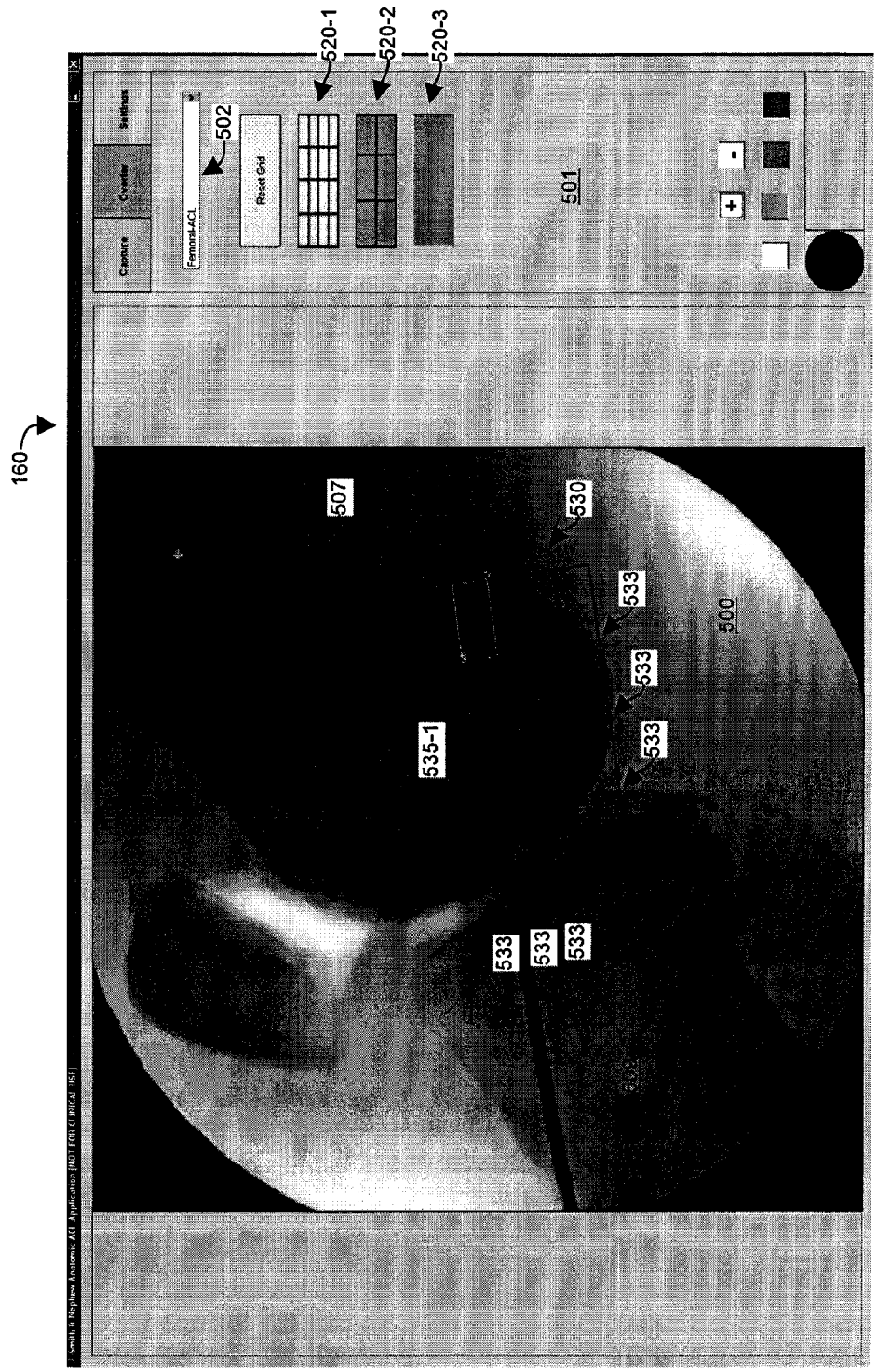

As shown in FIG. 8, the localization software 150 renders the graphical overlay 530 between the selected first known bone location 510-A and the selected second known bone location 511-A (and uses the third location 512-A for the femur). As shown, across its width and up and down its height, the graphical overlay 530 includes a series of guidance indicators 533 (grid lines in this example) operable to indicate positions (25% increments for overlay 520-1) associated to the anatomical structure for performing the surgical operation associated with the anatomical structure. The guidance indicators 533 for the first overlay grid are spaced at 25% increments across and down the geometry of the graphical overlay. This 25% overlay grid can be used to accurately place a required marker for marking a particular location on the femur associated with ACL repair. Other overlays (e.g. 520-2) can be used for placement of other markers used in this same surgery, as will be explained shortly.

After the overlay grid is displayed within the image area 500, the software 150 allows placement of localization markers within the overlay to indicate specific positions associated with a surgical or medical procedure in relation to the anatomical structure. As will be explained, placement of the localization markers can be manual via using a pointer and selecting a location within the overlay, or can be automated based on known locations for specific surgical procedures and anatomical structures, as dictated by the anatomical structure selected at location 502 in the graphical user interface 160.

In step 209 the localization software 150 displays at least one localization marker 535-1 within the graphical overlay 530. The localization marker 535-1 identifies a location for performing a surgical operation associated with the anatomical structure (e.g. the femur 507 in this example).

In sub-step 210, the localization software 150 receives manual input from a medical professional, such as the surgeon via an input device of the graphical user interface, to indicate a position (e.g. 25% over and down from the upper right corner) within the overlay grid 530 for placement of the localization marker based on a geometry of the overlay grid. This allows the surgeon to manually select where the localization marker 535-1 is to be placed.

In sub-step 211, in response to the input from the medical professional such as the release or click of a mouse button, the localization software 150 displays a respective localization marker 535-1 at each indicated position within the overlay grid 530.

In sub-step 212, for automatic placement of localization markers, the localization software 150 automatically calculates at least one medically preferred position (e.g. 25% over and down from landmark location 511-A) within the overlay grid 530 for placement of the localization marker based on a geometry of the overlay grid (and based on the selected anatomical structure to which the landmark location and overlay grid 530 are to be applied).

In sub-step 213, the localization software 150 displays a respective localization marker 535-1 at each automatically calculated medically preferred position within the overlay grid 530.

In sub-step 214, the localization software 150 allows a medical professional to adjust the automatically calculated placement of a respective localization marker within the overlay grid, if necessary.

Figure 9:
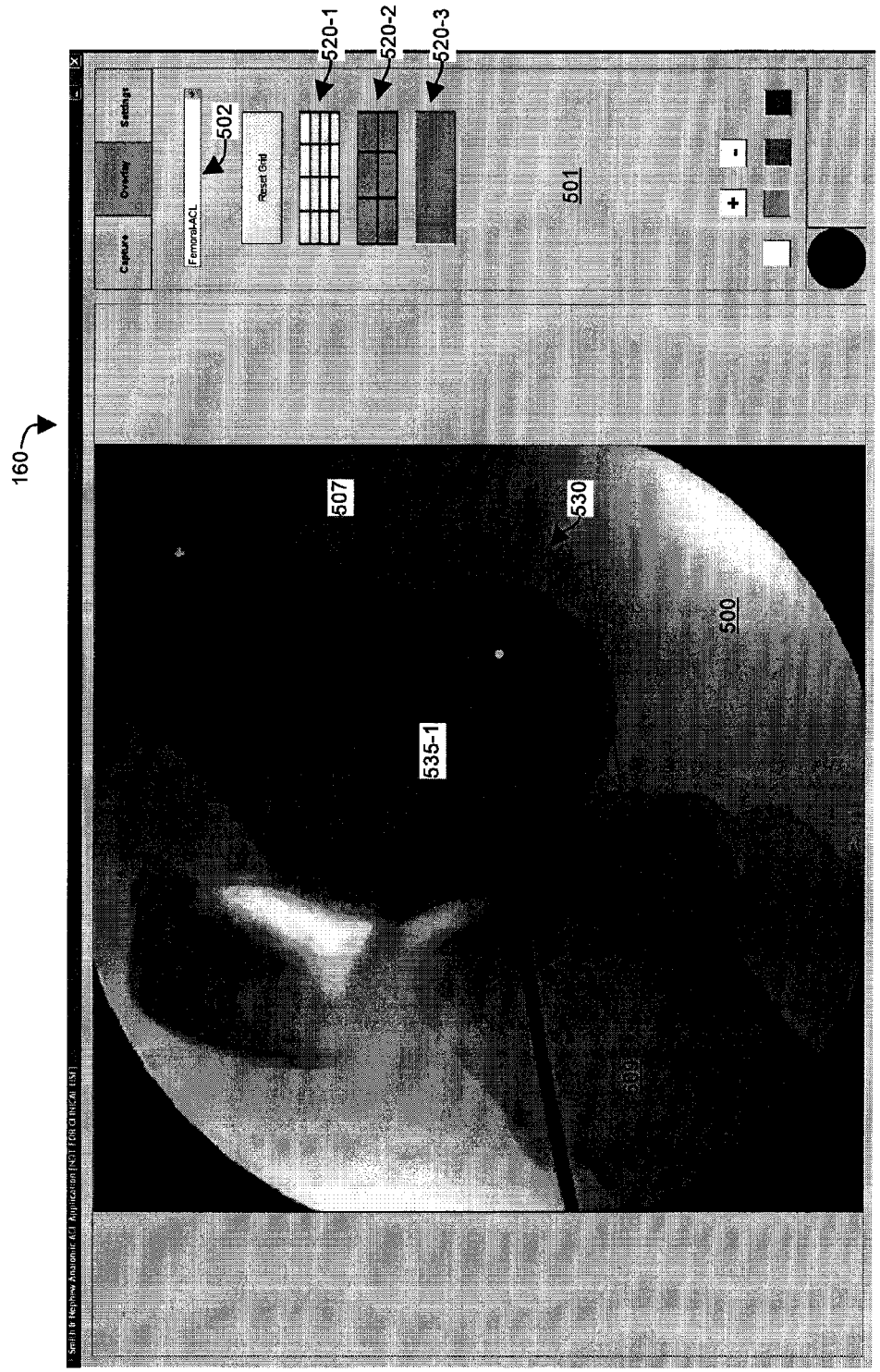

As shown in FIG. 9, after the surgeon selects a specific location for the localization marker within the overlay grid 530, the localization marker is highlighted in bold to indicate its exact position relative to the underlying image of the femur 507. In this manner, the localization software 150 displays at least one femoral localization marker within the overlay grid that identifies a reference location for a tissue graft insertion within the femur displayed within the graphical image. In a typical graft insertion, the surgeon is required to identify a second localization marker in relation to the femur. To do so, the surgeon can utilize a second overlay grid 520-2 that has a slightly different set of visualization guides or guidance indicators 533 that are spaced at different intervals (e.g. 33% increments across and 50% increments down, as opposed to 25% increments for grid 520-1). In other words, the system utilizes or provides a respective overlay grid 520 to position each respective localization marker for the tissue graft insertion site and the surgeon can select a specific grid 520 depending upon what localization marker is being placed (e.g. double bundle, single bundle, etc.). Each respective overlay grid (e.g. 520-1 and 520-2) includes a set of visual guidance indicators 533 that divide that respective overlay grid into different regions for proper positioning of that respective localization marker. Note to transition between different overlay grids 520, the surgeon can select a different grid 520 and the image area 500 will redisplay the newly selected grid within the selected landmark locations 510-A, 511-A and 512-A.

Figure 10:
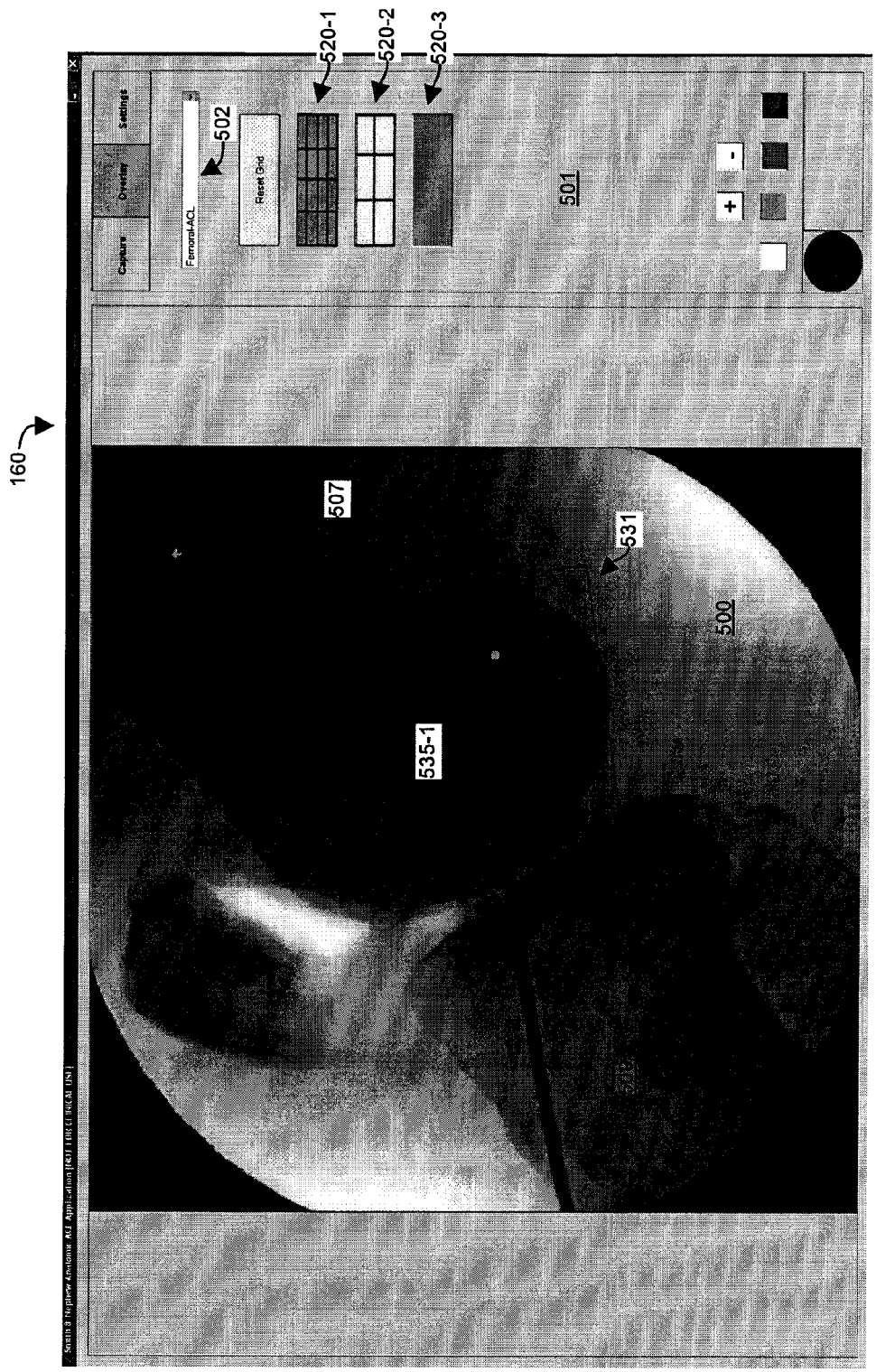

In step 215 and as shown in FIG. 10, the localization software 150 receives a selection of a second graphical overlay 520-2 from the plurality of available graphical overlays 520. As noted above, this second overlay 520-2 has guidance indicators spaced at different intervals (e.g. dividing the height and width of the overlay into thirds) than the overlay 520-1. The software 150 displays the selected second graphical overlay 520-2 as an overlay grid 531.

Figure 11:
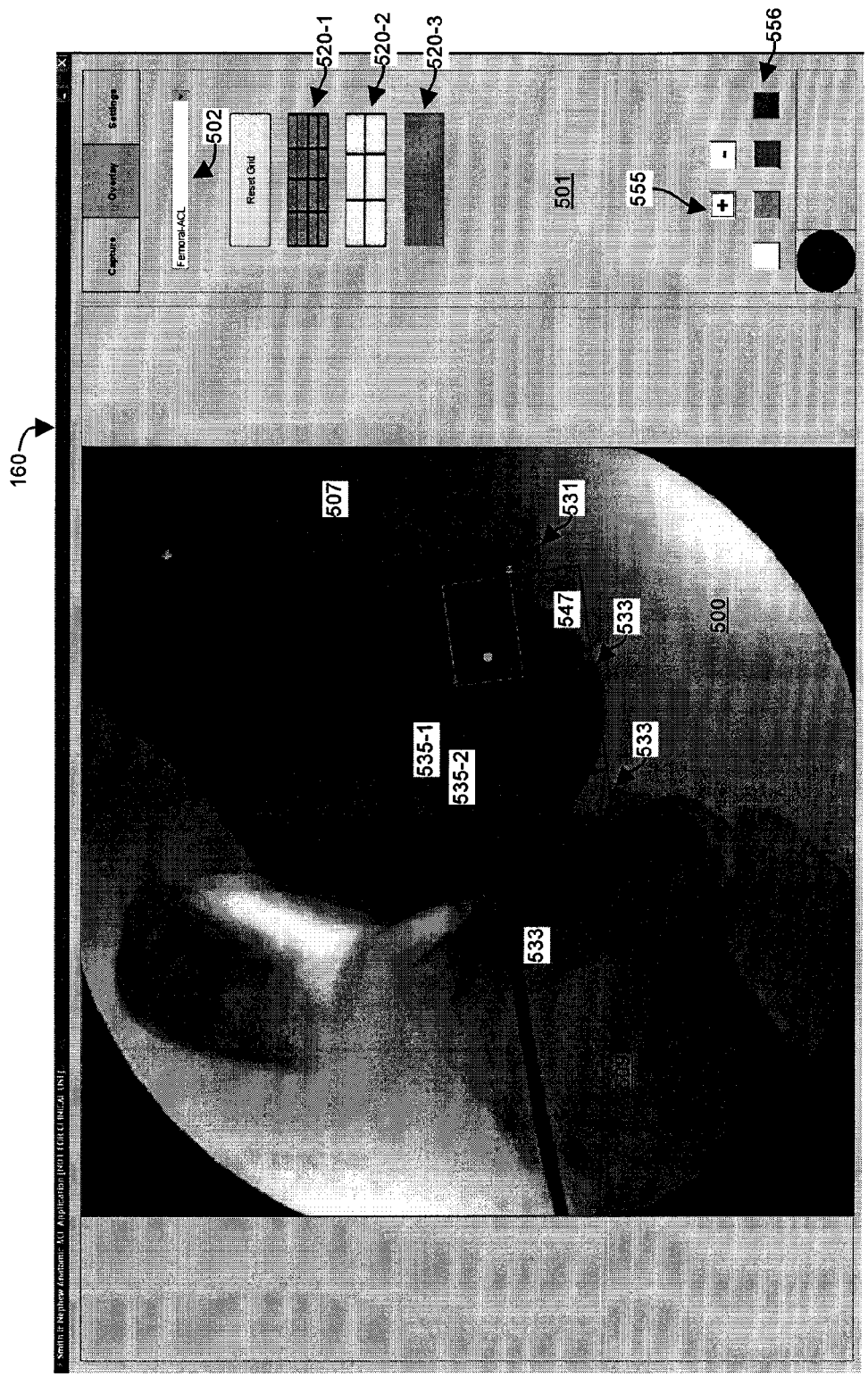

In step 216 and as shown in FIG. 11, the localization software 150 receives input from the medical professional, via an input device of the graphical user interface, to indicate a position 535-2 within the second displayed graphical overlay 531 for placement of a second localization marker 535-2 based on the series of guidance indicators 533 provided by the second graphical overlay 531. In particular, the operator such as the surgeon can select a marker addition function 555 (and a optionally a color 556 for the new marker) to indicate to the software that another localization marker 535 is to be added to the image area 500. Thereafter, when the surgeon moves the input device (e.g. mouse pointer) over the image graphical overlay 531, the relative position of the mouse pointer within the overlay is displayed next to the mouse pointer. As an example, after selecting the marker addition function 555, the first localization marker 535-1 is locked in place (displayed as a color dot 535-1 in this example) and as the mouse moves around grid 531 in FIG. 11 (or in another one of any selected overlay grids 520-1, 520-2, etc. that may be selected), the localization software 150 displays coordinates of the mouse pointer for precise placement of a second marker 535-2. In the example in FIG. 11, the software 150 can display a dotted line or reticule 547 (a rectangular box that tracks the mouse and is sized according to mouse movement within the overlay grid 531) to indicate mouse position within the displayed overlay grid 531. At the specific location of the mouse pointer itself, the software 150 can display across and down coordinate values in percentage values displayed in parenthesis such as (36%, 27%) to indicate the precise mouse location within the grid 531. As the mouse moves, these percentage value change and follow the mouse pointer. When the mouse is properly positioned (e.g. at location 33%, 50% for proper marker placement of the Posteriolateral (PL) bundle), the surgeon can click the mouse button and the second marker will be displayed. In this manner, the software 150 allows the surgeon to place a plurality of markers 535 within the image area 500. Placement of different marker can utilize the same of a different graphical overlay 520.

Figure 12:
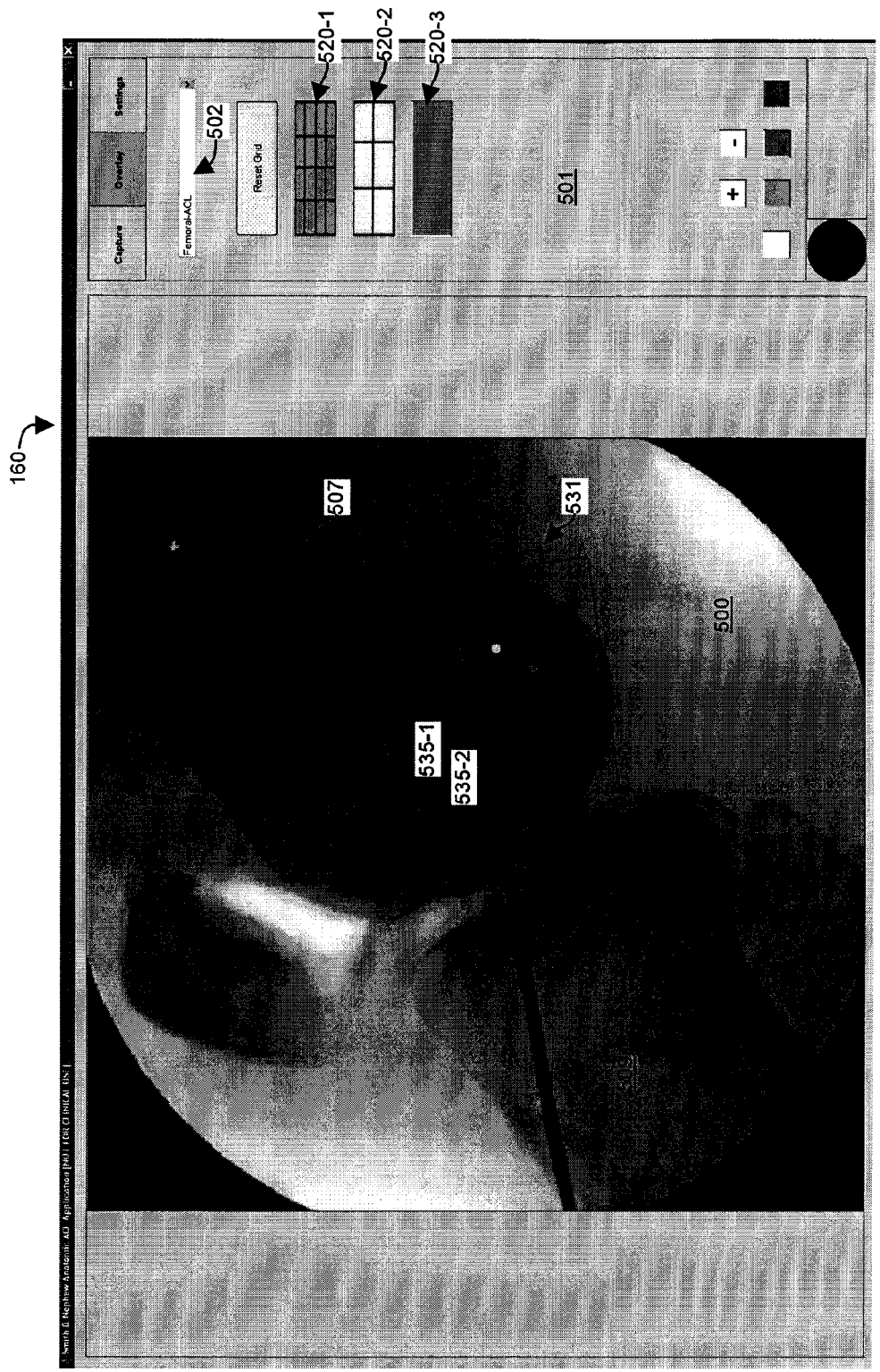

In step 217 and as shown in FIG. 12, in response to the second input (e.g. a positioning of the mouse at a desired location and a mouse press as explained above) from the medical professional, the localization software 150 displays a respective second localization marker 535-2 at the indicated position within the second graphical overlay 531. In this manner, the surgeon is able to place multiple localization markers 535-1 and 535-2 at specific locations in relation to the femur to visualize tissue graft insertion locations.

Figure 13:
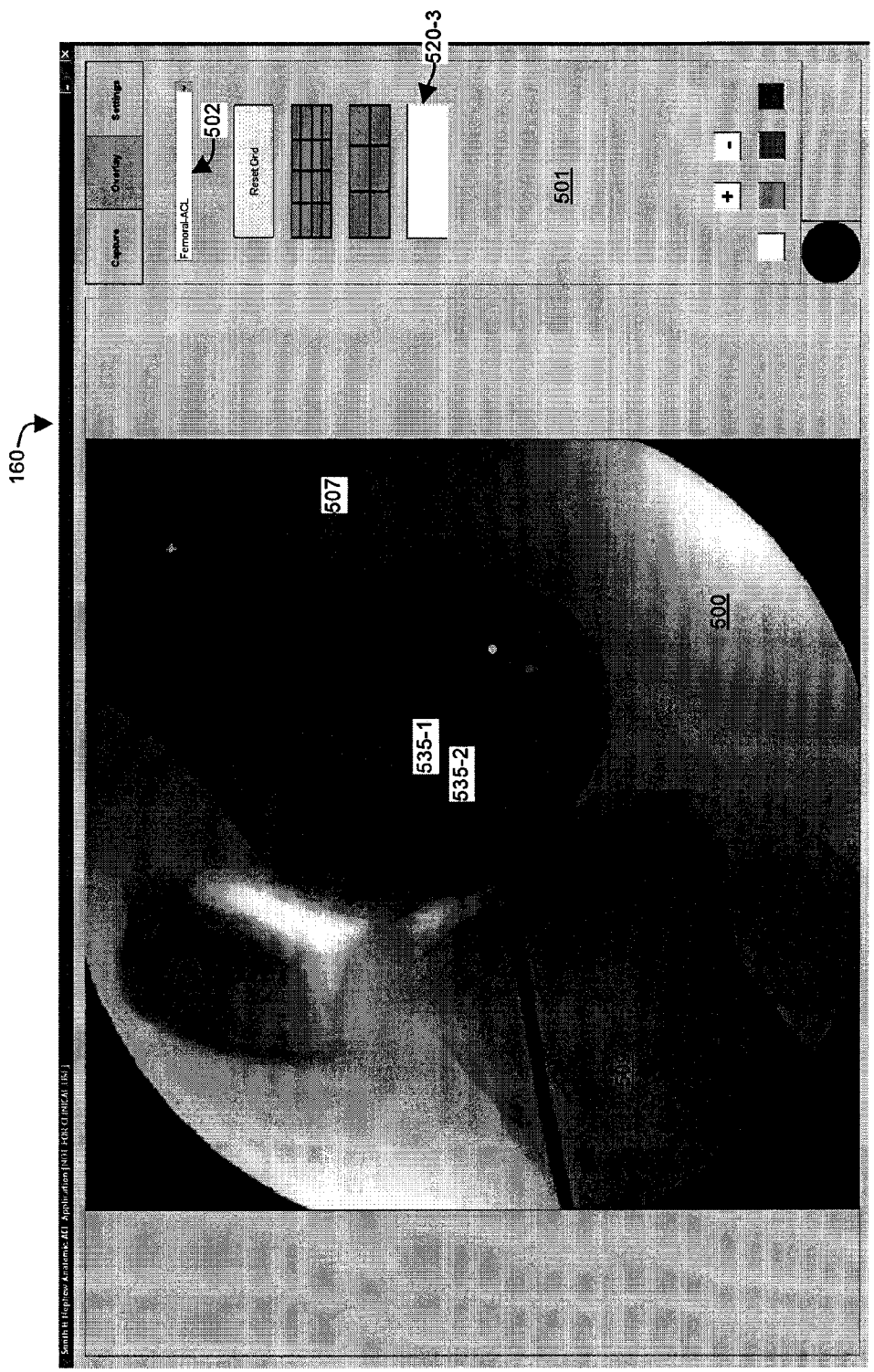

As shown in FIG. 13, after the surgeon has completed marking locations in relation to the femur as explained above, he or she can select the clear grid overlay 520-3 to remove the overlay grid 531 form the image view 500 in order to see an unobstructed view of the two marked locations 535-1 and 535-2.

At this point, using an endoscopic view (not shown in this example), the surgeon can physically adjust the position of a radiographically opaque to position a portion of the awl such as a tip closer in proximity to the localization marker(s) 535-1 and 535-2 that were established using the graphical overlays 520 in the above technique. Upon acquiring an image in the image area 500 that shows the awl, the surgeon can continue to position the tip of the awl to be close relative to the placed markers 535.

After marking the femur is complete as explained above, the surgeon can utilize the software 150 to also provide reference locations in relation to the tibia as explained below. Generally the process explained above for the femur is similar for the tibia except for the tibia, only two known tibia bone landmark locations are required to be selected in relation to the tibia. Based on these two landmark locations or known tibia bone locations, the placement of tibia localization markers can be performed on a graphical overlay that extends between the two landmarks.

Figure 14:
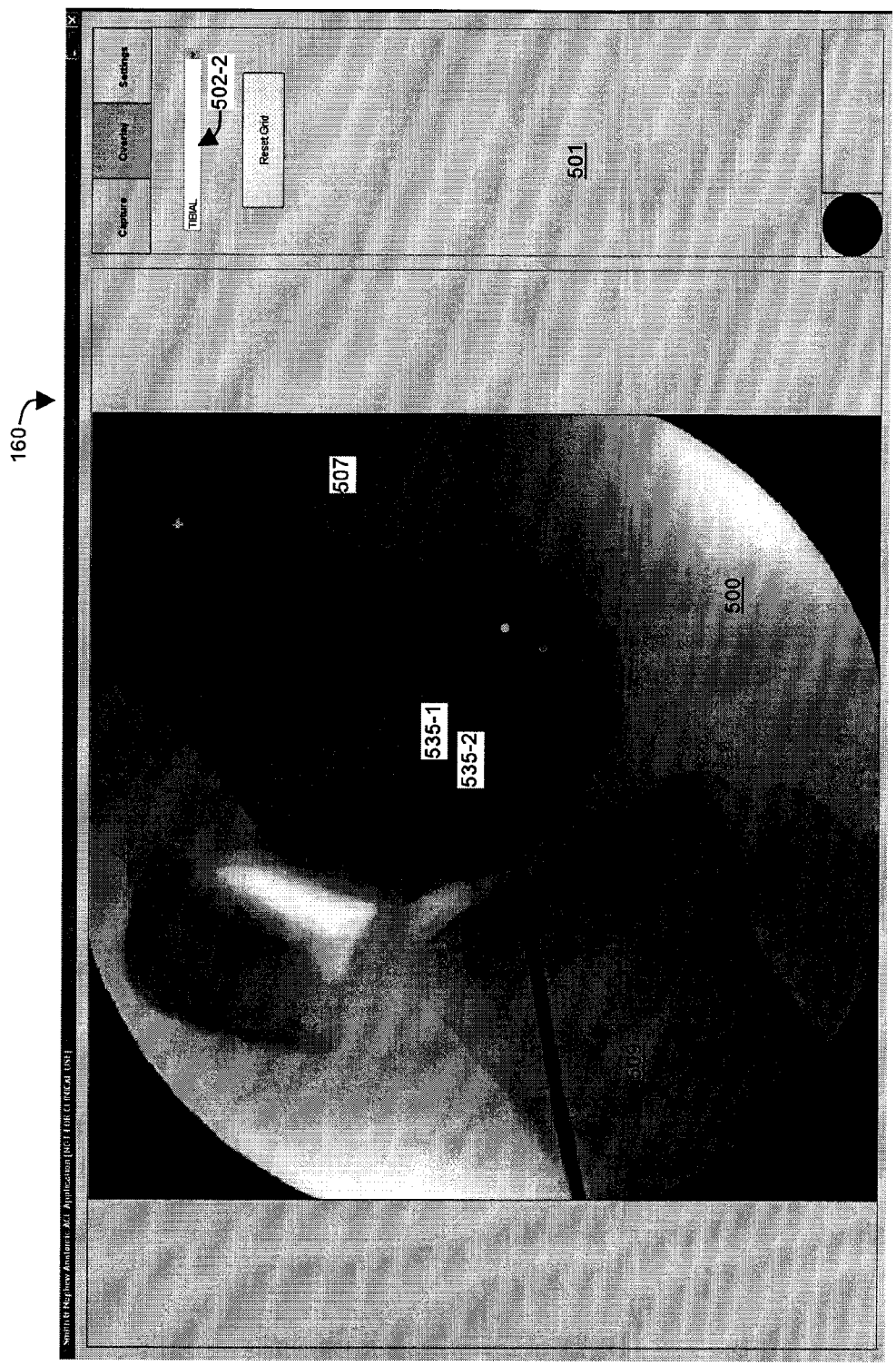

In step 218 and as shown in FIG. 14, the localization software 150 receives an anatomical structure selection 502 of a tibial anatomical structure (502-2 in FIG. 14) to which one or more landmark locations are to be provided. In this example, the surgeon has used the pull-down menu to select the "TIBIAL" structure 502-2 and as such, the localization software is configured to receive a selection of two known bone locations for the tibia 509 displayed within the image area 500. Note that upon selection of the TIBIAL structure 502-2, the overlay grid selections 520 do not appear, since only two landmark locations are required and the graphical overlay for the tibia is an overlay line between the two landmark locations, as opposed to the grid used for the femur.

Figure 15:
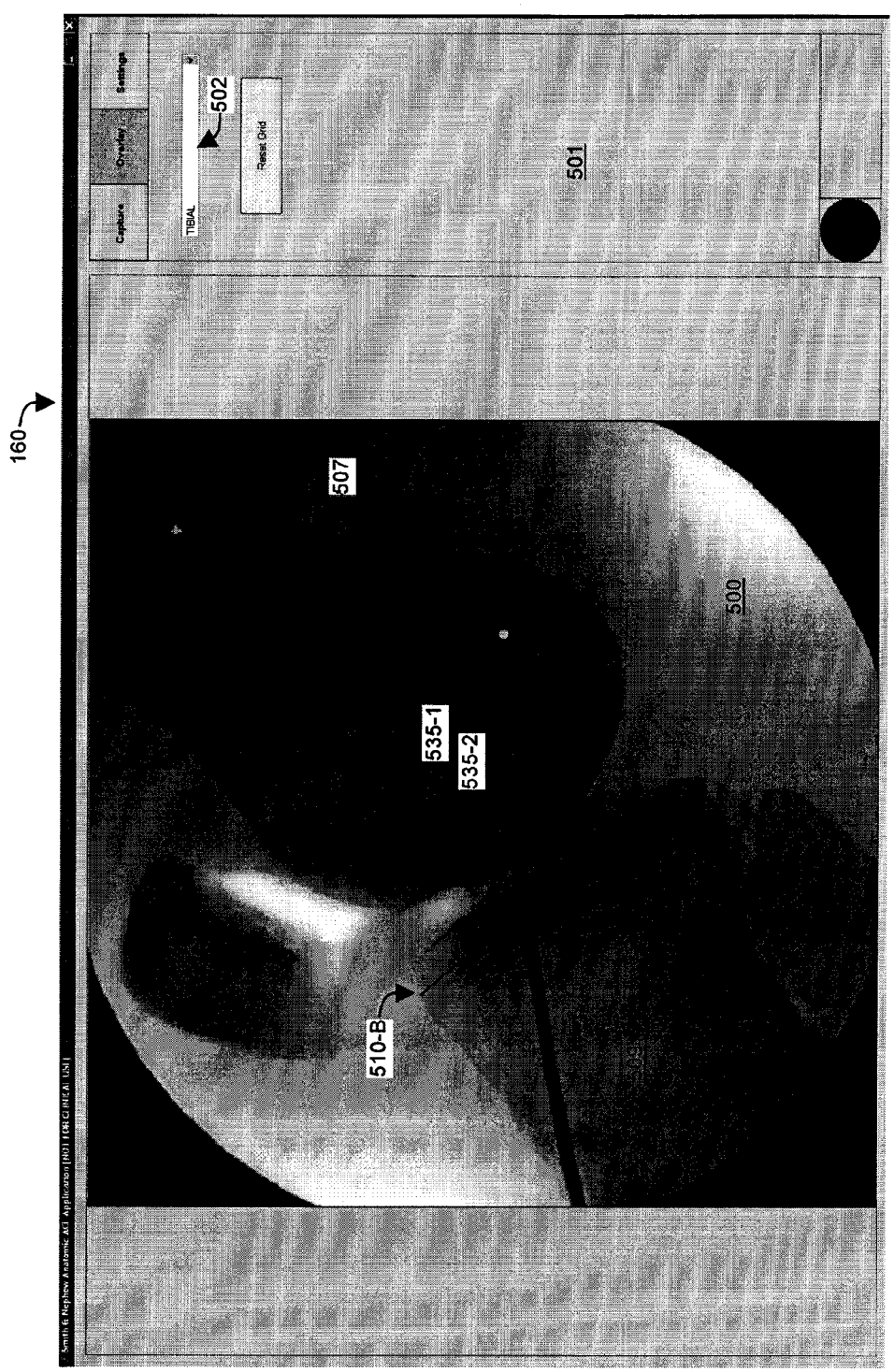

In step 219 and as shown in FIG. 15 the localization software 150 receives, as the first known bone location 510-B, a selection of an anterior edge of the view of the tibia displayed within the image 500. As was done above in relation to the femur, the surgeon can use a pointer device (e.g. mouse pointer and mouse click in the graphical user interface 160) to select the first landmark location 510-B for the tibia in this manner. Once selected, the graphical overlay appears and follows the pointer to the next landmark location.

Figure 16:
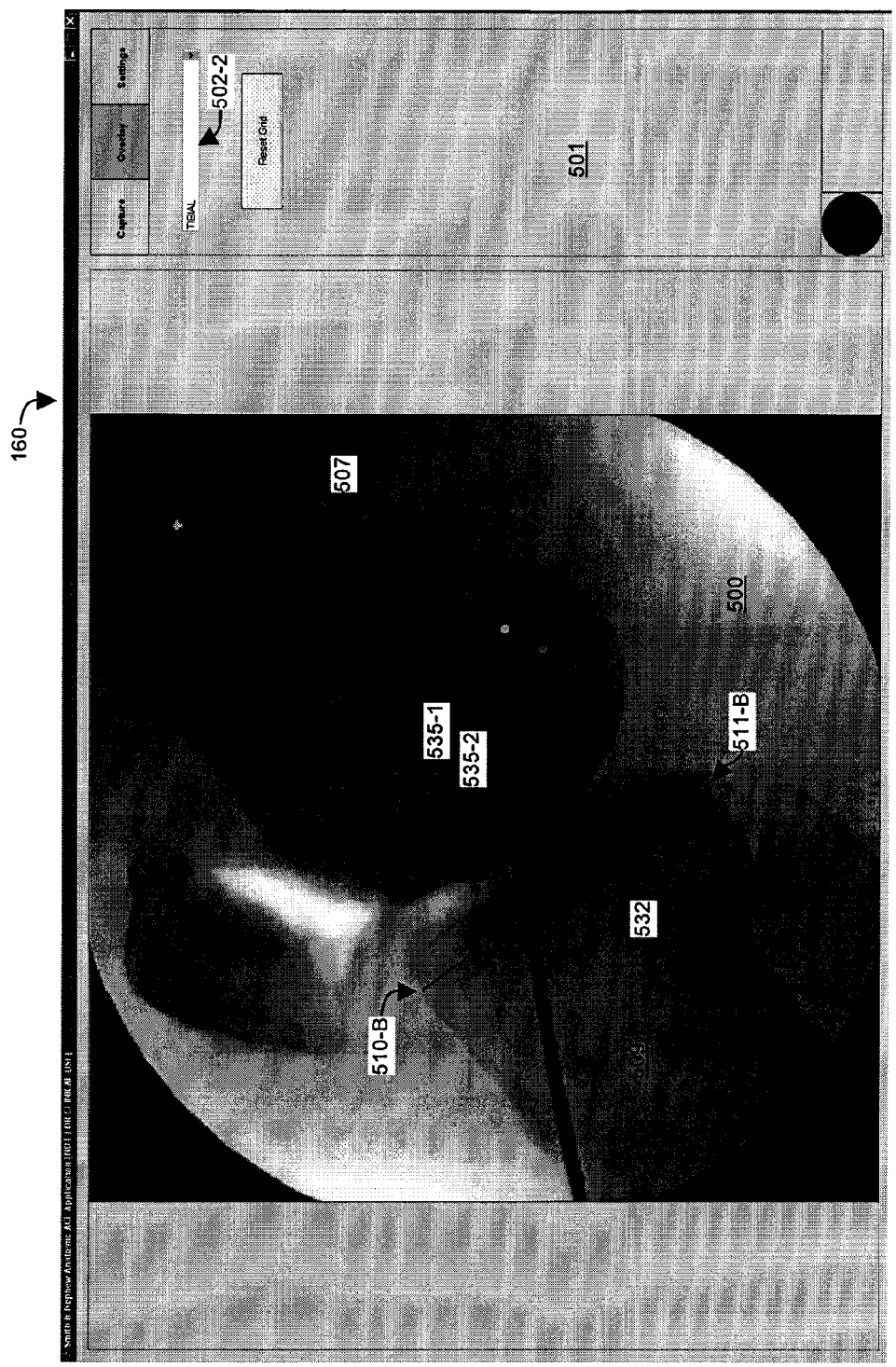

In step 220 and as shown in FIG. 16, the localization software 150 receives, as the second known bone location 511-B, a selection of a posterior edge of the view of the tibia displayed laterally within the image. The second known bone location selected by the surgeon is the second landmark location 511-B.

Figure 17:
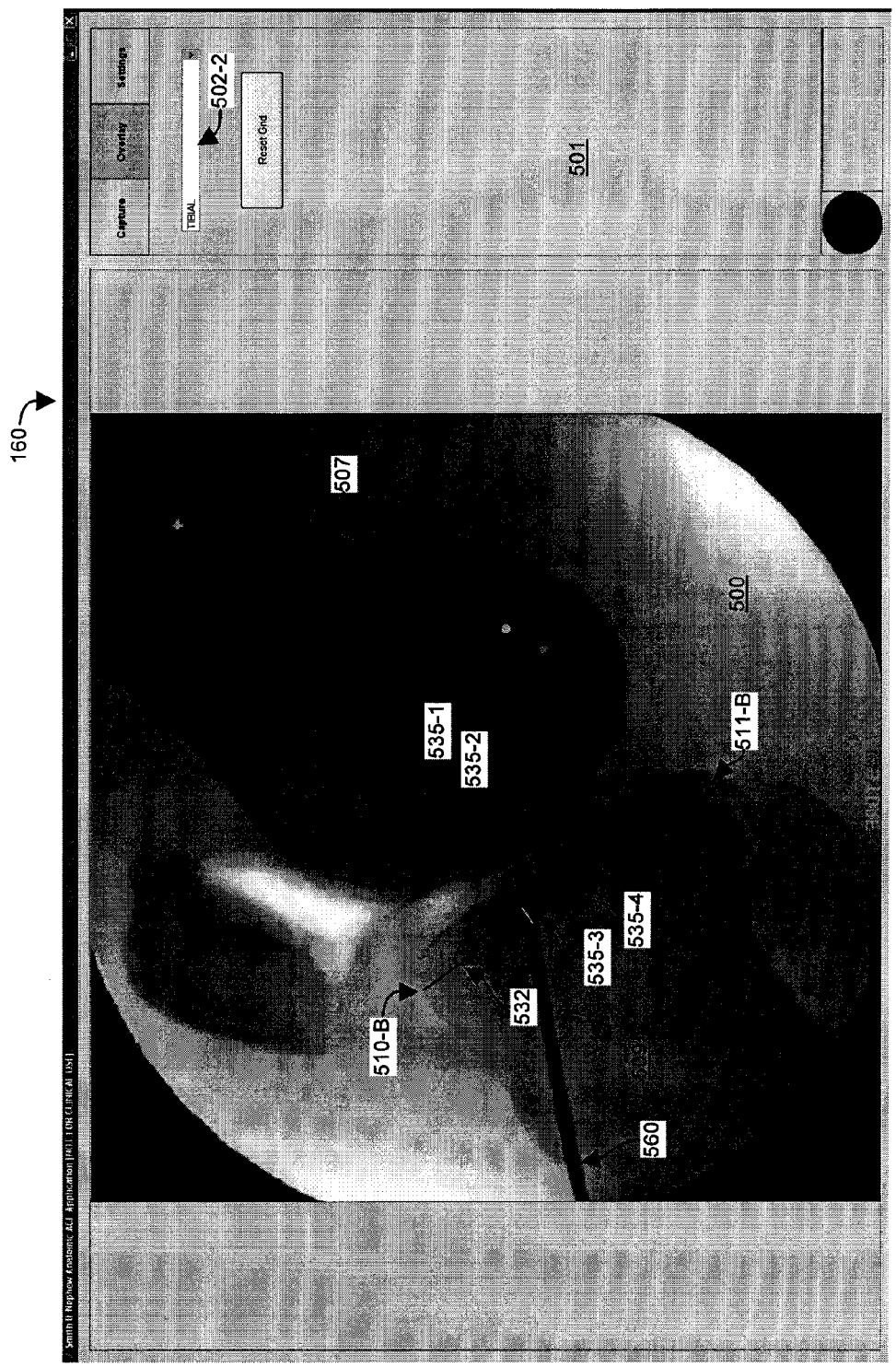

In step 221 and as shown in FIG. 17, the localization software 150 displays a graphical overlay as an overlay line 532 over the view of the proximal end of the tibia within the graphical user interface. The overlay line 532 extends between the selected first and second known bone locations (i.e. landmarks 510-B and 511-B) of the tibia. The graphical overlay shown as an overlay line 532 defined between the first known bone location or landmark 510-B and the second known bone location or landmark 511-B defines a plane upon which at least one localization marker (535-3 and 535-4 in FIG. 17) can be displayed for repair of a ligament (e.g. an ACL) associated to the tibia 509.

In step 222 the localization software 150 displays at least one tibia localization marker 535-3 and 535-4 located upon the overlay line 532. The tibia localization markers 535-3 and 535-4 identify at least one anatomic tissue graft insertion site on the tibia displayed within the graphical user interface 160.

Note that the specific placement of the tibia localization markers 535-3 and 535-4 can be automatic based on medically accepted locations (e.g. percentage distances) between the landmark locations 510-B and 5110B, or alternatively, the surgeon may manually place such localization markers 535-3 and 535-4 on the overlay line 532. If the software 150 places the markers 535-3 and 535-4, the surgeon can utilize the interface to select and move a specific marker 535 (this is also the case for the femur markers 535-1 and 535-2), if necessary. At this time, the location markers 535-3, 535-4 can be used to verify proper placement of a guidewire 560 used during ACL repair surgery and to confirm alignment of drilling locations. ACL repair is then continued according to standard medical procedures.

In an alternative configuration, the placement of the landmark locations 510 and/or related localization markers 535 for one anatomical structure (e.g. a bone such as the tibia) may be based on prior determination of landmark locations and/or localization markers 535 for a related anatomical structure, such as another bone (e.g. the femur). That is, in one alternative configuration, once the surgeon has utilized the system disclosed herein for placement of localization markers 535 for the femur (by way of example only), the tibia marker can be automatically placed. The software 150 can provide this functionality, for example, by being preprogrammed with standardized offsets, locations, or distances from known bone locations. In other alternative embodiments, the software 150 can utilize edge detection technology to automatically identify the landmark locations for both the femur and the tibia, and once these landmarks are located, the software 150 can utilize the known offsets for locations of the marker 535. In such embodiments for example, the localization software 150 is thus able to compute placement of at least one tibia localization marker based upon placement of the femoral localization marker(s) previously positioned within a femur overlay grid. In other alternative embodiments, the overlay grids can be selected while being displayed within the image view 500 and can be rotated, translated or resized as may be required by the surgeon's preference. To do so, the surgeon may use the pointing device (e.g. mouse pointer) to select the displayed grid (e.g. 530, 531) and once selected, the surgeon can grab a corner and rotate, resize or translate the overlay grid.

In other alternative embodiments, the system can incorporate the use of endoscopic equipment by, for example, transmitting and displaying the localization marker positions onto the endoscopic view for direct intraoperative localization of the insertion sites by a camera control unit (CCU) of an endoscopic system used in ACL repair procedures. To do so, the CCU could project, onto an image seen from a camera view of an endoscope, the grid overlays 530 and/or 531 as well as the positions of the markers 535. The overlay and marker positions can be computed, for example, based on relative angle information between the endoscopic camera and guidewire positions. In other alternative embodiments, the initial placement of the graphical overlays can be computed based on automatic detection of anatomical structure features using techniques such as edge detection or radio opaque place markers.

While computer systems, software, graphical user interfaces and data processing methods have been particularly shown and described above with references to configurations thereof, it will be understood by those skilled in the art that various changes in form and details may be made therein without departing from the scope disclosed herein. Accordingly, embodiments disclosed herein are not intended to be limited by the example configurations provided above.

What is claimed is:

1. A computer system comprising:
   a processing mechanism;
   an applications program for execution on the processing mechanism, which when executed on the processing mechanism yields a provides a localization software process; and
   wherein said applications program includes software code including data and logic instructions, where the software code, data and logic instructions are configured and arranged so as to perform operations of:
   displaying, on a graphical user interface, an image of an anatomical structure;
   identifying, via an input device on the graphical user interface, a set of landmark locations identifying respective anatomical positions within the displayed image of the anatomical structure;
   displaying a graphical overlay over the image of the anatomical structure, placement of the graphical overlay based on the set of landmark locations; and
   displaying at least one localization marker within the graphical overlay, the at least one localization marker identifying a location for performing a surgical operation associated with the anatomical structure;
   wherein the software code, data and logic instructions are further configured and arranged so that:
   such displaying an image of an anatomical structure further includes performing the operation(s) of displaying an image of the anatomical structure, the image including an image of at least one bone;
   such identifying a set of landmark locations further includes performing the operation(s) of receiving a structure selection of a specific anatomical structure to which landmark locations are to be provided, the structure selection defining a number of landmark locations to be identified, and receiving a selection, via a graphical pointer on the graphical user interface, of a first known bone location and a second known bone location associated with the at least one bone;
   such displaying a graphical overlay over the image of the anatomical structure further includes performing the operation(s) of rendering the graphical overlay between the selected first known bone location and the selected second known bone location, the graphical overlay including a series of guidance indicators operable to indicate positions associated to the anatomical structure for performing the surgical operation associated with the anatomical structure;
   such displaying an image of the anatomical structure further includes performing the operation(s) of displaying, on the graphical user interface, an image of a knee joint including a graphical view of a femur and tibia; and where such displaying a graphical overlay over the image of the anatomical structure further includes performing the operation(s) of displaying the graphical overlay over the view of at least one of the femur and the tibia within the image, the graphical overlay enabling ease of determination of at least one reference location to be marked by the at least one localization marker for performing a surgical operation related to repair of a ligament of the human knee joint;
   such displaying an image showing a view of a femur and tibia within a human knee joint further includes performing the operation(s) of displaying a lateral view of the femur within a human knee joint;
   such receiving a selection of first and second known bone locations further includes performing the operation(s) of receiving, as the first known bone location, a selection of an anterior edge of the view of the femur displayed within the image; receiving, as the second known bone location, a selection of a posterior edge of the view of the femur displayed laterally within the image, a line defined between the first known bone location and the second known bone location defining a plane that substantially aligns with a patellar surface of the femur; and further performing the operation(s) of receiving a selection of a third known bone location corresponding to the laterally displayed distal condyle surface of the femur within the image; and
   such displaying a graphical overlay over the image of the anatomical structure further includes performing the operation(s) of displaying an overlay grid over the view of the distal end of the femur within the graphical user interface, the overlay grid having a width rendered between the selected first and second known bone locations, and having a height that extends to the selected third known bone location.

2. The computing system of claim 1, wherein the software code, data and logic instructions are further configured and arranged so that such displaying at least one localization marker further includes performing the operation(s) of displaying at least one femoral localization marker within the overlay grid, the femoral localization marker identifying a reference location for a tissue graft insertion within the femur displayed within the graphical image.

3. The computing system of claim 2, wherein the software code, data and logic instructions are further configured and arranged so that such displaying at least one localization marker further includes performing the operation(s) of automatically calculating at least one medically preferred position within the overlay grid for placement of the localization marker based on a geometry of the overlay grid; and displaying a respective localization marker at each automatically calculated medically preferred position within the overlay grid.

4. The computing system of claim 3, wherein the software code, data and logic instructions are further configured and arranged for performing the operation(s) of allowing a medical professional to adjust the automatically calculated placement of a respective localization marker within the overlay grid.

5. The computing system of claim 2, wherein the software code, data and logic instructions are further configured and arranged so that such displaying at least one localization marker further includes performing the operation(s) of receiving manual input from a medical professional, via an input device of the graphical user interface, to indicate a position within the overlay grid for placement of the localization marker based on a geometry of the overlay grid; and in response to the received manual input from the medical professional, displaying a respective localization marker at each indicated position within the overlay grid.

6. The computing system of claim 1, wherein the software code, data and logic instructions are further configured and arranged so that such displaying an image showing a view of a femur and tibia within a human knee joint further includes performing the operation(s) of displaying a lateral view of the tibia within a human knee joint; where receiving a selection of first and second known bone locations further includes performing the operation(s) of receiving, as the first known bone location, a selection of an anterior edge of the view of the tibia displayed within the image; and receiving, as the second known bone location, a selection of a posterior edge of the view of the tibia displayed laterally within the image, a line defined between the first known bone location and the second known bone location defining a plane upon which the at least one localization marker can be displayed for repair of a ligament associated to the tibia.

7. The computing system of claim 6, wherein the software code, data and logic instructions are further configured and arranged so that such displaying a graphical overlay over the image of the anatomical structure further includes performing the operation(s) of displaying an overlay line between the select first and second known bone locations of the tibia; and where such displaying at least one localization marker within the graphical overlay further includes displaying at least one tibia localization marker located upon the overlay line, the at least one tibia localization marker identifying at least one anatomic ACL insertion site on the tibia displayed within the graphical user interface.

8. The computing system of claim 7, wherein the software code, data and logic instructions are further configured and arranged so that such displaying at least one tibia localization marker located upon the overlay line further includes performing the operation(s) of computing placement of the at least one tibia localization marker based upon placement of the at least one femoral localization marker previously positioned within a femur overlay grid, the femoral localization marker identifying a reference location for a tissue graft insertion site within a femur displayed within the graphical image.

9. The computing system of claim 1, wherein the software code, data and logic instructions are further configured and arranged so as to further perform the operation(s) of:
based on placement of the at least one localization marker within the graphical overlay, computing placement of localization markers for at least one other anatomical structure, and displaying the localization markers for at least one other anatomical structure within the displayed image within the graphical user interface.

10. The computing system of claim 1, wherein the software code, data and logic instructions are further configured and arranged so that such displaying a graphical overlay over the image of the anatomical structure further includes performing the operation(s) of:
displaying a plurality of selectable graphical overlays within the graphical user interface, each graphical overlay within the plurality of selectable graphical overlays providing a respective series of guidance indicators operable to indicate positions associated to the anatomical structure for performing a respective portion of the surgical operation associated with the anatomical structure;
receiving a selection of a first graphical overlay from a plurality of available graphical overlays, and
wherein such displaying at least one localization marker within the graphical overlay further includes performing the operation(s) of:
receiving first input from a medical professional, via an input device of the graphical user interface, to indicate a position within the first graphical overlay for placement of a first localization marker based on the series of guidance indicators provided by the first graphical overlay; and
in response to the input from the medical professional, displaying a respective first localization marker at the indicated position within the first graphical overlay.

11. The computing system of claim 10, wherein the software code, data and logic instructions are further configured and arranged so t as to perform the operation(s) of:
receiving a selection of a second graphical overlay from a plurality of available graphical overlays,
receiving second input from a medical professional, via an input device of the graphical user interface, to indicate a position within the second graphical overlay for placement of a second localization marker based on the series of guidance indicators provided by the second graphical overlay; and
in response to the second input from the medical professional, displaying a respective second localization marker at the indicated position within the second graphical overlay.

12. The computing system of claim 1, wherein the software code, data and logic instructions are further configured and arranged so that:
the operations of identifying a set of landmark locations include performing the operation(s) of displaying a graphical overlay and displaying at least one localization marker within the graphical overlay are performed a first time for a first set of localization markers for a femoral ACL insertion site; and
the operations of identifying a set of landmark locations, include performing the operation(s) of displaying a graphical overlay and displaying at least one localization marker within the graphical overlay are performed a second time for a second set of localization markers for a tibial ACL insertion site.

13. The computing system of claim 12, wherein the software code, data and logic instructions are further configured and arranged so that:
the operations of identifying a set of landmark locations, include performing the operation(s) of displaying a graphical overlay and displaying at least one localization marker within the graphical overlay are performed a first time for a first set of localization markers for a femoral ACL insertion site; and
the software code, data and logic instructions are further configured and arranged so as to further perform the operation(s) of utilizing a respective overlay grid to position each respective localization marker for the femoral ACL insertion site, each respective overlay grid including visual guidance indicators that divide that respective overlay grid into different regions for proper positioning of that respective localization marker.

14. The computing system of claim 1, wherein the software code, data and logic instructions are further configured and arranged so thatsuch displaying the graphical user interface includes performing the operation(s) of displaying at least a portion of the graphical user interface within an endoscopic view.

15. The computing system of claim 1, wherein the software code, data and logic instructions are further configured and arranged so as to perform the operation(s) of displaying the at least one localization marker within an endoscopic view.

16. The computing system of claim 1, wherein the software code, data and logic instructions are further configured and arranged so that such displaying the at least one localization marker within the graphical overlay includes performing the operation(s) of generating at least one landmark location based at least in part on at least one anatomical characteristic detected in the image of the anatomical structure.

17. The computing system of claim 16, wherein the software code, data and logic instructions are further configured and arranged so that such generating the at least one landmark location based at least in part on at least one anatomical characteristic detected in the image of the anatomical structure includes performing the operation(s) of:

detecting at least one edge portion of the anatomical structure in the image of the anatomical structure; and determining at least one landmark position in the anatomical structure with respect to a measurement based at least in part on the at least one detected edge portion.

18. The computing system of claim 1, wherein the software code, data and logic instructions are further configured and arranged so that such displaying of at least one localization marker within the graphical overlay includes performing the operation(s) of displaying a series of guidance indicators operable to indicate positions associated to the anatomical structure for performing the surgical operation associated with the anatomical structure.

19. The computing system of claim 18, wherein the software code, data and logic instructions are further configured and arranged so that such guidance indicators indicate at least one percentage position, the percentage position providing at least one of a scale and a metric based on a distance between the landmark locations of the bone.

20. The computing system of claim 1, wherein the software code, data and logic instructions are further configured and arranged so that such displaying at least one localization marker within the graphical overlay includes performing the operation(s) of displaying at least one guidance indicator identifying a metric based on respective landmark locations, the guidance indicator further describing a position on the anatomical structure relevant to a surgical operation.

21. The computer system of claim 1, further comprising:
a memory;
an interconnection mechanism that operably couples the memory and the processing mechanism; and
wherein the memory is encoded with the applications program that when executed on the processor provides the localization software process.

22. The computer system of claim 1, further comprising:
a storage medium;
wherein the interconnection mechanism operably couples the memory, the processing mechanism and the storage medium; and
wherein the applications program is stored in the storage medium.

23. A non-transitory computer readable medium on which is stored an applications program that when executed as a process in a computing mechanism produces a localization software process, wherein said applications program includes software code including data and logic instructions, where the software code, data and logic instructions are configured and arranged so as to perform operations of:
displaying, on a graphical user interface, an image of an anatomical structure;
identifying, via an input device on the graphical user interface, a set of landmark locations identifying respective anatomical positions within the displayed image of the anatomical structure;
displaying a graphical overlay over the image of the anatomical structure, placement of the graphical overlay based on the set of landmark locations; and
displaying at least one localization marker within the graphical overlay, the at least one localization marker identifying a location for performing a surgical operation associated with the anatomical structure;
wherein the software code, data and logic instructions are further configured and arranged so that:
such displaying an image of an anatomical structure further includes performing the operation(s) of displaying an image of the anatomical structure, the image including an image of at least one bone;
such identifying a set of landmark locations further includes performing the operation(s) of receiving a structure selection of a specific anatomical structure to which landmark locations are to be provided, the structure selection defining a number of landmark locations to be identified, and receiving a selection, via a graphical pointer on the graphical user interface, of a first known bone location and a second known bone location associated with the at least one bone;
such displaying a graphical overlay over the image of the anatomical structure further includes performing the operation(s) of rendering the graphical overlay between the selected first known bone location and the selected second known bone location, the graphical overlay including a series of guidance indicators operable to indicate positions associated to the anatomical structure for performing the surgical operation associated with the anatomical structure;
such displaying an image of the anatomical structure further includes performing the operation(s) of displaying, on the graphical user interface, an image of a knee joint including a graphical view of a femur and tibia; and where such displaying a graphical overlay over the image of the anatomical structure further includes performing the operation(s) of displaying the graphical overlay over the view of at least one of the femur and the tibia within the image, the graphical overlay enabling ease of determination of at least one reference location to be marked by the at least one localization marker for performing a surgical operation related to repair of a ligament of the human knee joint;
such displaying an image showing a view of a femur and tibia within a human knee joint further includes performing the operation(s) of displaying a lateral view of the femur within a human knee joint;
such receiving a selection of first and second known bone locations further includes performing the operation(s) of receiving, as the first known bone location, a selection of an anterior edge of the view of the femur displayed within the image; receiving, as the second known bone location, a selection of a posterior edge of the view of the femur displayed laterally within the image, a line defined between the first known bone location and the second known bone location defining a plane that substantially aligns with a patellar surface of the femur; and further performing the operation(s) of receiving a selection of a third known bone location corresponding to the laterally displayed distal condyle surface of the femur within the image; and
such displaying a graphical overlay over the image of the anatomical structure further includes performing the operation(s) of displaying an overlay grid over the view of the distal end of the femur within the graphical user interface, the overlay grid having a width rendered between the selected first and second known bone locations, and having a height that extends to the selected third known bone location.

24. The non-transitory computer readable medium of claim 23, wherein the software code, data and logic instructions are further configured and arranged so that such displaying at least one localization marker further includes performing the operation(s) of displaying at least one femoral localization marker within the overlay grid, the femoral localization marker identifying a reference location for a tissue graft insertion within the femur displayed within the graphical image.

25. The non-transitory computer readable medium of claim 24, wherein the software code, data and logic instructions are further configured and arranged so that such displaying at least one localization marker further includes performing the operation(s) of automatically calculating at least one medically preferred position within the overlay grid for placement of the localization marker based on a geometry of the overlay grid; and displaying a respective localization marker at each automatically calculated medically preferred position within the overlay grid.

26. The non-transitory computer readable medium of claim 25, wherein the software code, data and logic instructions are further configured and arranged for performing the operation(s) of allowing a medical professional to adjust the automatically calculated placement of a respective localization marker within the overlay grid.

27. The non-transitory computer readable medium of claim 24, wherein the software code, data and logic instructions are further configured and arranged so that such displaying at least one localization marker further includes performing the operation(s) of receiving manual input from a medical professional, via an input device of the graphical user interface, to indicate a position within the overlay grid for placement of the localization marker based on a geometry of the overlay grid; and in response to the received manual input from the medical professional, displaying a respective localization marker at each indicated position within the overlay grid.

28. The non-transitory computer readable medium of claim 23, wherein the software code, data and logic instructions are further configured and arranged so that such displaying an image showing a view of a femur and tibia within a human knee joint further includes performing the operation(s) of displaying a lateral view of the tibia within a human knee joint; where receiving a selection of first and second known bone locations further includes performing the operation(s) of receiving, as the first known bone location, a selection of an anterior edge of the view of the tibia displayed within the image; and receiving, as the second known bone location, a selection of a posterior edge of the view of the tibia displayed laterally within the image, a line defined between the first known bone location and the second known bone location defining a plane upon which the at least one localization marker can be displayed for repair of a ligament associated to the tibia.

29. The non-transitory computer readable medium of claim 28, wherein the software code, data and logic instructions are further configured and arranged so that such displaying a graphical overlay over the image of the anatomical structure further includes performing the operation(s) of displaying an overlay line between the select first and second known bone locations of the tibia; and where such displaying at least one localization marker within the graphical overlay further includes displaying at least one tibia localization marker located upon the overlay line, the at least one tibia localization marker identifying at least one anatomic ACL insertion site on the tibia displayed within the graphical user interface.

30. The non-transitory computer readable medium of claim 29, wherein the software code, data and logic instructions are further configured and arranged so that such displaying at least one tibia localization marker located upon the overlay line further includes performing the operation(s) of computing placement of the at least one tibia localization marker based upon placement of the at least one femoral localization marker previously positioned within a femur overlay grid, the femoral localization marker identifying a reference location for a tissue graft insertion site within a femur displayed within the graphical image.

31. The non-transitory computer readable medium of claim 23, wherein the software code, data and logic instructions are further configured and arranged so as to further perform the operation(s) of:
based on placement of the at least one localization marker within the graphical overlay, computing placement of localization markers for at least one other anatomical structure, and displaying the localization markers for at least one other anatomical structure within the displayed image within the graphical user interface.

32. The non-transitory computer readable medium of claim 23, wherein the software code, data and logic instructions are further configured and arranged so that such displaying a graphical overlay over the image of the anatomical structure further includes performing the operation(s) of:
displaying a plurality of selectable graphical overlays within the graphical user interface, each graphical overlay within the plurality of selectable graphical overlays providing a respective series of guidance indicators operable to indicate positions associated to the anatomical structure for performing a respective portion of the surgical operation associated with the anatomical structure;
receiving a selection of a first graphical overlay from a plurality of available graphical overlays, and
wherein such displaying at least one localization marker within the graphical overlay further includes performing the operation(s) of:
receiving first input from a medical professional, via an input device of the graphical user interface, to indicate a position within the first graphical overlay for placement of a first localization marker based on the series of guidance indicators provided by the first graphical overlay; and
in response to the input from the medical professional, displaying a respective first localization marker at the indicated position within the first graphical overlay.

33. The non-transitory computer readable medium of claim 32, wherein the software code, data and logic instructions are further configured and arranged so t as to perform the operation(s) of:
receiving a selection of a second graphical overlay from a plurality of available graphical overlays,
receiving second input from a medical professional, via an input device of the graphical user interface, to indicate a position within the second graphical overlay for placement of a second localization marker based on the series of guidance indicators provided by the second graphical overlay; and
in response to the second input from the medical professional, displaying a respective second localization marker at the indicated position within the second graphical overlay.

34. The non-transitory computer readable medium of claim 23, wherein the software code, data and logic instructions are further configured and arranged so that:
the operations of identifying a set of landmark locations include performing the operation(s) of displaying a graphical overlay and displaying at least one localization marker within the graphical overlay are performed a first time for a first set of localization markers for a femoral ACL insertion site; and
the operations of identifying a set of landmark locations, include performing the operation(s) of displaying a graphical overlay and displaying at least one localization marker within the graphical overlay are performed a second time for a second set of localization markers for a tibial ACL insertion site.

35. The non-transitory computer readable medium of claim 34, wherein the software code, data and logic instructions are further configured and arranged so that:

the operations of identifying a set of landmark locations, include performing the operation(s) of displaying a graphical overlay and displaying at least one localization marker within the graphical overlay are performed a first time for a first set of localization markers for a femoral ACL insertion site; and the software code, data and logic instructions are further configured and arranged so as to further perform the operation(s) of utilizing a respective overlay grid to position each respective localization marker for the femoral ACL insertion site, each respective overlay grid including visual guidance indicators that divide that respective overlay grid into different regions for proper positioning of that respective localization marker.

36. The non-transitory computer readable medium of claim 23, wherein the software code, data and logic instructions are further configured and arranged so that such displaying the graphical user interface includes performing the operation(s) of displaying at least a portion of the graphical user interface within an endoscopic view.

37. The non-transitory computer readable medium of claim 23, wherein the software code, data and logic instructions are further configured and arranged so as to perform the operation(s) of displaying the at least one localization marker within an endoscopic view.

38. The non-transitory computer readable medium of claim 23, wherein the software code, data and logic instructions are further configured and arranged so that such displaying the at least one localization marker within the graphical overlay includes performing the operation(s) of generating at least one landmark location based at least in part on at least one anatomical characteristic detected in the image of the anatomical structure.

39. The non-transitory computer readable medium of claim 38, wherein the software code, data and logic instructions are further configured and arranged so that such generating the at least one landmark location based at least in part on at least one anatomical characteristic detected in the image of the anatomical structure includes performing the operation(s) of:

detecting at least one edge portion of the anatomical structure in the image of the anatomical structure; and determining at least one landmark position in the anatomical structure with respect to a measurement based at least in part on the at least one detected edge portion.

40. The non-transitory computer readable medium of claim 23, wherein the software code, data and logic instructions are further configured and arranged so that such displaying of at least one localization marker within the graphical overlay includes performing the operation(s) of displaying a series of guidance indicators operable to indicate positions associated to the anatomical structure for performing the surgical operation associated with the anatomical structure.

41. The non-transitory computer readable medium of claim 40, wherein the software code, data and logic instructions are further configured and arranged so that such guidance indicators indicate at least one percentage position, the percentage position providing at least one of a scale and a metric based on a distance between the landmark locations of the bone.

42. The non-transitory computer readable medium of claim 23, wherein the software code, data and logic instructions are further configured and arranged so that such displaying at least one localization marker within the graphical overlay includes performing the operation(s) of displaying at least one guidance indicator identifying a metric based on respective landmark locations, the guidance indicator further describing a position on the anatomical structure relevant to a surgical operation.

* * * * *